US010202586B2

(12) United States Patent
Park et al.

(10) Patent No.: US 10,202,586 B2
(45) Date of Patent: Feb. 12, 2019

(54) DEHALOGENASE VARIANT PROTEIN, POLYNUCLEOTIDE ENCODING DEHALOGENASE VARIANT PROTEIN, RECOMBINANT MICROORGANISM INCLUDING POLYNUCLEOTIDE, COMPOSITION INCLUDING RECOMBINANT MICROORGANISM, AND METHOD OF REDUCING CONCENTRATION OF FLUORINATED METHANE USING DEHALOGENASE

(71) Applicant: Samsung Electronics Co., Ltd, Suwon-si, Gyeonggi-do (KR)

(72) Inventors: Joonsong Park, Seoul (KR); Taeyong Kim, Daejeon (KR); Jinhwan Park, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 15/783,592

(22) Filed: Oct. 13, 2017

(65) Prior Publication Data

US 2018/0105803 A1 Apr. 19, 2018

(30) Foreign Application Priority Data

Oct. 13, 2016 (KR) ........................ 10-2016-0133076

(51) Int. Cl.

| | |
|---|---|
| ***C12N 9/14*** | (2006.01) |
| ***B01D 53/70*** | (2006.01) |
| ***B01D 53/84*** | (2006.01) |

(52) U.S. Cl.

CPC ............... *C12N 9/14* (2013.01); *B01D 53/70* (2013.01); *B01D 53/84* (2013.01); *C12Y 308/01005* (2013.01); *B01D 2255/804* (2013.01); *B01D 2257/2066* (2013.01); *B01D 2258/0216* (2013.01)

(58) Field of Classification Search

CPC .. C12N 9/14; C12Y 308/01005; B01D 53/84; B01D 53/70; B01D 2255/804

See application file for complete search history.

(56) References Cited

U.S. PATENT DOCUMENTS

2016/0333359 A1 11/2016 Song et al.

FOREIGN PATENT DOCUMENTS

EP 3178922 A1 6/2017

OTHER PUBLICATIONS

Witkowski et al., Biochemistry 38:11643-11650, 1999.*
Seffernick et al., J. Bacteriol. 183(8):2405-2410, 2001.*
Sadowski et al., Current Opinion in Structural Biology 19:357-362, 2009.*
Branden et al., Introduction to Protein Structure, Garland Publishing Inc., New York, p. 247, 1991.*
GenBank accession No. WP_054721235, Oct. 15, 2015.*
Bagnoud et al., GenBank accession No. KUO60930, Jan. 15, 2016.*
Kruse et al., GenBank accession No. AHF10423, May 14, 2014.*
Cao, J., GenBank accession No. AMK11019, Feb. 18, 2016.*
Justicia-Leon et al., "Dichloromethane Fermentation by a *Dehalobacter* sp. in an Enrichment Culture Derived from Pristine River Sediment", *Applied and Environmental Microbiology*, 78(4): 1288-1291 (2012).
Manchester et al., "Enzyme-catalyzed dehalogenation of pentachloroethane: why F87W-cytochrome P450cam is faster than wild type", *Protein Engineering*, 8(8): 801-807, (1995).
Tang et al., "Identification of *Dehalobacter* reductive dehalogenases that catalyse dechlorination of chloroform, 1,1,1-trichloroethane and 1,1-dichloroethane", *Philosophical Transactions of the Royal Society B*, 368: Mar. 18, 2012, 1-10 (2013).
Tang et al., "Sister *Dehalobacter* Genomes Reveal Specialization in Organohalide Respiration and Recent Strain Differentiation Likely Driven by Chlorinated Substrates", *Frontiers in Microbiology*, 7(100): 1-14 (2016).
Chen et al. "Directed Evolution of Cytochrome P450 for Small Alkane Hydroxylation," *Thesis, California Institute of Technology* (2011).

* cited by examiner

*Primary Examiner* — Delia M Ramirez
(74) *Attorney, Agent, or Firm* — Leydig, Voit & Mayer, Ltd.

(57) ABSTRACT

Provided are a dehalogenase variant, a polynucleotide encoding the dehalogenase variant, a recombinant microorganism including a genetic modification that increases dehalogenase activity, a composition including the recombinant microorganism, and a method of reducing a concentration of fluorinated methane using the recombinant microorganism.

7 Claims, 3 Drawing Sheets

Specification includes a Sequence Listing.

SEQUENCE LISTING

<160> NUMBER OF SEQ ID NOS: 112

<210> SEQ ID NO 1
<211> LENGTH: 456
<212> TYPE: PRT
<213> ORGANISM: Artificial Sequence
<220> FEATURE:
<223> OTHER INFORMATION: Synthetic chloroform reductive dehalogenase (CfrA)

<400> SEQUENCE: 1

Met Asp Lys Glu Lys Ser Asn Asn Asp Lys Pro Ala Thr Lys Ile Asn
1 5 10 15

Arg Arg Gln Phe Leu Lys Phe Gly Ala Gly Ala Ser Ser Gly Ile Ala
20 25 30

Ile Ala Thr Ala Ala Thr Ala Leu Gly Gly Lys Ser Leu Ile Asp Pro
35 40 45

Lys Gln Val Tyr Ala Gly Thr Val Lys Glu Leu Asp Glu Leu Pro Phe
50 55 60

Asn Ile Pro Ala Asp Tyr Lys Pro Phe Thr Asn Gln Arg Asn Ile Tyr
65 70 75 80

Gly Gln Ala Val Leu Gly Val Pro Glu Pro Leu Ala Leu Val Glu Arg
85 90 95

Phe Asp Glu Val Arg Trp Asn Gly Trp Gln Thr Asp Gly Ser Pro Gly
100 105 110

Leu Thr Val Leu Asp Gly Ala Ala Ala Arg Ala Ser Phe Ala Val Asp
115 120 125

Tyr Tyr Phe Asn Gly Glu Asn Ser Ala Cys Arg Ala Asn Lys Gly Phe
130 135 140

Phe Glu Trp His Pro Lys Val Ala Glu Leu Asn Phe Lys Trp Gly Asp
145 150 155 160

Pro Glu Arg Asn Ile His Ser Pro Gly Val Lys Ser Ala Glu Glu Gly
165 170 175

Thr Met Ala Val Lys Lys Ile Ala Arg Phe Phe Gly Ala Ala Lys Ala
180 185 190

Gly Ile Ala Pro Phe Asp Lys Arg Trp Val Phe Thr Glu Thr Tyr Ala
195 200 205

Phe Val Lys Thr Pro Glu Gly Glu Ser Leu Lys Phe Ile Pro Pro Asp
210 215 220

Phe Gly Phe Glu Pro Lys His Val Ile Ser Met Ile Ile Pro Gln Ser
225 230 235 240

Pro Glu Gly Val Lys Cys Asp Pro Ser Phe Leu Gly Ser Thr Glu Tyr
245 250 255

Gly Leu Ser Cys Ala Gln Ile Gly Tyr Ala Ala Phe Gly Leu Ser Met
260 265 270

Phe Ile Lys Asp Leu Gly Tyr His Ala Val Pro Ile Gly Ser Asp Ser
275 280 285

Ala Leu Ala Ile Pro Ile Ala Ile Gln Ala Gly Leu Gly Glu Tyr Ser
290 295 300

Arg Ser Gly Leu Met Ile Thr Pro Glu Phe Gly Ser Asn Val Arg Leu
305 310 315 320

Cys Glu Val Phe Thr Asp Met Pro Leu Asn His Asp Lys Pro Ile Ser
325 330 335

Phe Gly Val Thr Glu Phe Cys Lys Thr Cys Lys Lys Cys Ala Glu Ala
340 345 350

-continued

Cys Ala Pro Gln Ala Ile Ser Tyr Glu Asp Pro Thr Ile Asp Gly Pro
355 360 365

Arg Gly Gln Met Gln Asn Ser Gly Ile Lys Arg Trp Tyr Val Asp Pro
370 375 380

Val Lys Cys Leu Glu Phe Met Ser Arg Asp Asn Val Gly Asn Cys Cys
385 390 395 400

Gly Ala Cys Ile Ala Ala Cys Pro Phe Thr Lys Pro Glu Ala Trp His
405 410 415

His Thr Leu Ile Arg Ser Leu Val Gly Ala Pro Val Ile Thr Pro Phe
420 425 430

Met Lys Asp Met Asp Asp Ile Phe Gly Tyr Gly Lys Leu Asn Asp Glu
435 440 445

Lys Ala Ile Ala Asp Trp Trp Lys
450 455

<210> SEQ ID NO 2
<211> LENGTH: 1371
<212> TYPE: DNA
<213> ORGANISM: Artificial Sequence
<220> FEATURE:
<223> OTHER INFORMATION: Synthetic chloroform reductive dehalogenase (CfrA)

<400> SEQUENCE: 2
atggacaaag agaaatccaa caacgacaaa ccggcgacca agatcaaccg ccgccagttc 60
ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatcg cgcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggctaccac 840
gccgttccga ttggttctga cagcgccctg gccattccga ttgcgattca ggcgggtctg 900
ggcgaatatt ctcgttctgg cctgatgatt actccggaat ttggcagcaa cgttcgtctg 960
tgtgaagtgt ttacggatat gccgctgaac catgacaaac cgatctcctt cggcgttacc 1020
gaattctgta agacgtgcaa gaaatgcgcg gaagcgtgtg cgccgcaggc gatttcctat 1080
gaagacccga ccattgatgg cccgcgtggc cagatgcaga actccggcat caaacgctgg 1140
tatgttgatc cggtaaaatg tctggaattc atgtcccgcg ataatgttgg caattgctgc 1200
ggcgcgtgca ttgcggcgtg cccgtttacc aaaccggaag cgtggcatca caccctgatt 1260
cgctccctgg ttggcgcgcc ggttattacg ccgtttatga aagatatgga tgatatcttt 1320
ggctatggca aactgaatga tgagaaagcc atcgccgatt ggtggaaata g 1371

-continued

<210> SEQ ID NO 3
<211> LENGTH: 456
<212> TYPE: PRT
<213> ORGANISM: Artificial Sequence
<220> FEATURE:
<223> OTHER INFORMATION: Synthetic cfrA-A184W

<400> SEQUENCE: 3

```
Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Trp Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Tyr His Ala Val Pro Ile Gly Ser Asp Ser
        275                 280                 285

Ala Leu Ala Ile Pro Ile Ala Ile Gln Ala Gly Leu Gly Glu Tyr Ser
    290                 295                 300

Arg Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro

        355                 360                 365

Arg Gly Gln Met Gln Asn Ser Gly Ile Lys Arg Trp Tyr Val Asp Pro
```

-continued

```
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
    450                 455


<210> SEQ ID NO 4
<211> LENGTH: 456
<212> TYPE: PRT
<213> ORGANISM: Artificial Sequence
<220> FEATURE:
<223> OTHER INFORMATION: Synthetic cfrA Y279K

<400> SEQUENCE: 4

Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Lys His Ala Val Pro Ile Gly Ser Asp Ser
```

```
        275                 280                 285

Ala Leu Ala Ile Pro Ile Ala Ile Gln Ala Gly Leu Gly Glu Tyr Ser
    290                 295                 300

Arg Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro
        355                 360                 365

Arg Gly Gln Met Gln Asn Ser Gly Ile Lys Arg Trp Tyr Val Asp Pro
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
    450                 455


<210> SEQ ID NO 5
<211> LENGTH: 456
<212> TYPE: PRT
<213> ORGANISM: Artificial Sequence
<220> FEATURE:
<223> OTHER INFORMATION: Synthetic cfrA E302Q

<400> SEQUENCE: 5

Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
```

-continued

```
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Tyr His Ala Val Pro Ile Gly Ser Asp Ser
        275                 280                 285

Ala Leu Ala Ile Pro Ile Ala Ile Gln Ala Gly Leu Gly Gln Tyr Ser
    290                 295                 300

Arg Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro
        355                 360                 365

Arg Gly Gln Met Gln Asn Ser Gly Ile Lys Arg Trp Tyr Val Asp Pro
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
    450                 455


<210> SEQ ID NO 6
<211> LENGTH: 456
<212> TYPE: PRT
<213> ORGANISM: Artificial Sequence
<220> FEATURE:
<223> OTHER INFORMATION: Synthetic cfrA R305I

<400> SEQUENCE: 6

Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
```

-continued

```
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Tyr His Ala Val Pro Ile Gly Ser Asp Ser
        275                 280                 285

Ala Leu Ala Ile Pro Ile Ala Ile Gln Ala Gly Leu Gly Glu Tyr Ser
    290                 295                 300

Ile Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro
        355                 360                 365

Arg Gly Gln Met Gln Asn Ser Gly Ile Lys Arg Trp Tyr Val Asp Pro
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
    450                 455
```

<210> SEQ ID NO 7
<211> LENGTH: 1371
<212> TYPE: DNA
<213> ORGANISM: Artificial Sequence
<220> FEATURE:
<223> OTHER INFORMATION: Synthetic cfrA A184W -continued

<400> SEQUENCE: 7

```
atggacaaag agaaatccaa caacgacaaa ccggcgacca agatcaaccg ccgccagttc      60
ctgaaattcg gcgcaggtgc atctagcggt atcgctatcg caactgcagc aactgcactg     120
ggtggcaaat ccctgatcga tcctaaacag gtgtacgcag gtactgtgaa agagctggac     180
gagctgccgt tcaacatccc tgcagactac aaaccgttca ctaaccagcg taacatctac     240
ggccaggcag tactgggtgt acctgagcct ctggcactgg tagaacgctt tgacgaagta     300
cgttggaacg gttggcaaac tgacggttct ccaggtctga ccgttctgga tggtgcagct     360
gcgcgtgcta gctttgctgt tgattattac ttcaacggcg agaactctgc ttgccgtgct     420
aacaagggtt tcttcgagtg gcacccgaaa gtggctgaac tgaacttcaa atggggcgac     480
ccagaacgta acatccacag cccaggtgtc aaatccgctg aagaaggtac catggctgtg     540
aagaagatct ggcgtttctt cggtgctgct aaagcgggta tcgctccatt cgacaaacgt     600
tgggtcttca ccgaaaccta cgccttcgtg aagaccccag aaggtgaatc tctgaaattc     660
atcccgccgg acttcggctt cgaaccgaaa cacgttatca gcatgatcat cccgcagagc     720
ccggaaggtg tcaaatgcga cccgagcttt ctgggttcta ccgaatacgg tctgtcttgt     780
gctcaaatcg gttacgccgc cttcggtctg tctatgttca tcaaagacct gggctaccac     840
gccgttccga ttggttctga cagcgccctg gccattccga ttgcgattca ggcgggtctg     900
ggcgaatatt ctcgttctgg cctgatgatt actccggaat ttggcagcaa cgttcgtctg     960
tgtgaagtgt ttacggatat gccgctgaac catgacaaac cgatctcctt cggcgttacc    1020
gaattctgta agacgtgcaa gaaatgcgcg gaagcgtgtg cgccgcaggc gatttcctat    1080
gaagacccga ccattgatgg cccgcgtggc cagatgcaga actccggcat caaacgctgg    1140
tatgttgatc cggtaaaatg tctggaattc atgtcccgcg ataatgttgg caattgctgc    1200
ggcgcgtgca ttgcggcgtg cccgtttacc aaaccggaag cgtggcatca caccctgatt    1260
cgctccctgg ttggcgcgcc ggttattacg ccgtttatga aagatatgga tgatatcttt    1320
ggctatggca aactgaatga tgagaaagcc atcgccgatt ggtggaaata g             1371
```

<210> SEQ ID NO 8
<211> LENGTH: 1371
<212> TYPE: DNA
<213> ORGANISM: Artificial Sequence
<220> FEATURE:
<223> OTHER INFORMATION: Synthetic cfrA Y279K

<400> SEQUENCE: 8

```
atggacaaag agaaatccaa caacgacaaa ccggcgacca agatcaaccg ccgccagttc      60
ctgaaattcg gcgcaggtgc atctagcggt atcgctatcg caactgcagc aactgcactg     120
ggtggcaaat ccctgatcga tcctaaacag gtgtacgcag gtactgtgaa agagctggac     180
gagctgccgt tcaacatccc tgcagactac aaaccgttca ctaaccagcg taacatctac     240
ggccaggcag tactgggtgt acctgagcct ctggcactgg tagaacgctt tgacgaagta     300
cgttggaacg gttggcaaac tgacggttct ccaggtctga ccgttctgga tggtgcagct     360
gcgcgtgcta gctttgctgt tgattattac ttcaacggcg agaactctgc ttgccgtgct     420
aacaagggtt tcttcgagtg gcacccgaaa gtggctgaac tgaacttcaa atggggcgac     480
ccagaacgta acatccacag cccaggtgtc aaatccgctg aagaaggtac catggctgtg     540
aagaagatcg cgcgtttctt cggtgctgct aaagcgggta tcgctccatt cgacaaacgt     600
tgggtcttca ccgaaaccta cgccttcgtg aagaccccag aaggtgaatc tctgaaattc     660
```

atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggcaaacac 840
gccgttccga ttggttctga cagcgccctg gccattccga ttgcgattca ggcgggtctg 900
ggcgaatatt ctcgttctgg cctgatgatt actccggaat ttggcagcaa cgttcgtctg 960
tgtgaagtgt ttacggatat gccgctgaac catgacaaac cgatctcctt cggcgttacc 1020
gaattctgta agacgtgcaa gaaatgcgcg gaagcgtgtg cgccgcaggc gatttcctat 1080
gaagacccga ccattgatgg cccgcgtggc cagatgcaga actccggcat caaacgctgg 1140
tatgttgatc cggtaaaatg tctggaattc atgtcccgcg ataatgttgg caattgctgc 1200
ggcgcgtgca ttgcggcgtg cccgtttacc aaaccggaag cgtggcatca caccctgatt 1260
cgctccctgg ttggcgcgcc ggttattacg ccgtttatga aagatatgga tgatatcttt 1320
ggctatggca aactgaatga tgagaaagcc atcgccgatt ggtggaaata g 1371

<210> SEQ ID NO 9
<211> LENGTH: 1371
<212> TYPE: DNA
<213> ORGANISM: Artificial Sequence
<220> FEATURE:
<223> OTHER INFORMATION: Synthetic cfrA Y279K

<400> SEQUENCE: 9
atggacaaag agaaatccaa caacgacaaa ccggcgacca agatcaaccg ccgccagttc 60
ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatcg cgcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggcaagcac 840
gccgttccga ttggttctga cagcgccctg gccattccga ttgcgattca ggcgggtctg 900
ggcgaatatt ctcgttctgg cctgatgatt actccggaat ttggcagcaa cgttcgtctg 960
tgtgaagtgt ttacggatat gccgctgaac catgacaaac cgatctcctt cggcgttacc 1020
gaattctgta agacgtgcaa gaaatgcgcg gaagcgtgtg cgccgcaggc gatttcctat 1080
gaagacccga ccattgatgg cccgcgtggc cagatgcaga actccggcat caaacgctgg 1140
tatgttgatc cggtaaaatg tctggaattc atgtcccgcg ataatgttgg caattgctgc 1200
ggcgcgtgca ttgcggcgtg cccgtttacc aaaccggaag cgtggcatca caccctgatt 1260
cgctccctgg ttggcgcgcc ggttattacg ccgtttatga aagatatgga tgatatcttt 1320

-continued ggctatggca aactgaatga tgagaaagcc atcgccgatt ggtggaaata g 1371

<210> SEQ ID NO 10
<211> LENGTH: 1371
<212> TYPE: DNA
<213> ORGANISM: Artificial Sequence
<220> FEATURE:
<223> OTHER INFORMATION: Synthetic cfrA E302Q

<400> SEQUENCE: 10
atggacaaag agaaatccaa caacgacaaa ccggcgacca agatcaaccg ccgccagttc 60
ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatcg cgcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggctaccac 840
gccgttccga ttggttctga cagcgccctg gccattccga ttgcgattca ggcgggtctg 900
ggccaatatt ctcgttctgg cctgatgatt actccggaat ttggcagcaa cgttcgtctg 960
tgtgaagtgt ttacggatat gccgctgaac catgacaaac cgatctcctt cggcgttacc 1020
gaattctgta agacgtgcaa gaaatgcgcg gaagcgtgtg cgccgcaggc gatttcctat 1080
gaagacccga ccattgatgg cccgcgtggc cagatgcaga actccggcat caaacgctgg 1140
tatgttgatc cggtaaaatg tctggaattc atgtcccgcg ataatgttgg caattgctgc 1200
ggcgcgtgca ttgcggcgtg cccgtttacc aaaccggaag cgtggcatca caccctgatt 1260
cgctccctgg ttggcgcgcc ggttattacg ccgtttatga aagatatgga tgatatcttt 1320
ggctatggca aactgaatga tgagaaagcc atcgccgatt ggtggaaata g 1371

<210> SEQ ID NO 11
<211> LENGTH: 1371
<212> TYPE: DNA
<213> ORGANISM: Artificial Sequence
<220> FEATURE:
<223> OTHER INFORMATION: Synthetic cfrA E302Q

<400> SEQUENCE: 11
atggacaaag agaaatccaa caacgacaaa ccggcgacca agatcaaccg ccgccagttc 60
ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatcg cgcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggctaccac 840
gccgttccga ttggttctga cagcgccctg gccattccga ttgcgattca ggcgggtctg 900
ggccagtatt ctcgttctgg cctgatgatt actccggaat ttggcagcaa cgttcgtctg 960
tgtgaagtgt ttacggatat gccgctgaac catgacaaac cgatctcctt cggcgttacc 1020
gaattctgta agacgtgcaa gaaatgcgcg gaagcgtgtg cgccgcaggc gatttcctat 1080
gaagacccga ccattgatgg cccgcgtggc cagatgcaga actccggcat caaacgctgg 1140
tatgttgatc cggtaaaatg tctggaattc atgtcccgcg ataatgttgg caattgctgc 1200
ggcgcgtgca ttgcggcgtg cccgtttacc aaaccggaag cgtggcatca caccctgatt 1260
cgctccctgg ttggcgcgcc ggttattacg ccgtttatga aagatatgga tgatatcttt 1320
ggctatggca aactgaatga tgagaaagcc atcgccgatt ggtggaaata g 1371

<210> SEQ ID NO 12
<211> LENGTH: 1371
<212> TYPE: DNA
<213> ORGANISM: Artificial Sequence
<220> FEATURE:
<223> OTHER INFORMATION: Synthetic cfrA R305I

<400> SEQUENCE: 12
atggacaaag agaaatccaa caacgacaaa ccggcgacca agatcaaccg ccgccagttc 60
ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatcg cgcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggctaccac 840
gccgttccga ttggttctga cagcgccctg gccattccga ttgcgattca ggcgggtctg 900
ggcgaatatt ctatttctgg cctgatgatt actccggaat ttggcagcaa cgttcgtctg 960
tgtgaagtgt ttacggatat gccgctgaac catgacaaac cgatctcctt cggcgttacc 1020

-continued

```
gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 13
<211> LENGTH: 1371
<212> TYPE: DNA
<213> ORGANISM: Artificial Sequence
<220> FEATURE:
<223> OTHER INFORMATION: Synthetic cfrA R305I

<400> SEQUENCE: 13

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120

ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420

aacaagggtt tcttcgagtg gcacccgaaa gtggctgaac tgaacttcaa atggggcgac    480

ccagaacgta acatccacag cccaggtgtc aaatccgctg aagaaggtac catggctgtg    540

aagaagatcg cgcgtttctt cggtgctgct aaagcgggta tcgctccatt cgacaaacgt    600

tgggtcttca ccgaaaccta cgccttcgtg aagaccccag aaggtgaatc tctgaaattc    660

atcccgccgg acttcggctt cgaaccgaaa cacgttatca gcatgatcat cccgcagagc    720

ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840

gccgttccga ttggttctga cagcgccctg gccattccga ttgcgattca ggcgggtctg    900

ggcgaatatt ctatctctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 14
<211> LENGTH: 1371
<212> TYPE: DNA
<213> ORGANISM: Artificial Sequence
<220> FEATURE:
<223> OTHER INFORMATION: Synthetic cfrA R305I

<400> SEQUENCE: 14

```
atggacaaag agaaatccaa caacgacaaa ccggcgacca agatcaaccg ccgccagttc     60
```

-continued ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatcg cgcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggctaccac 840
gccgttccga ttggttctga cagcgccctg gccattccga ttgcgattca ggcgggtctg 900
ggcgaatatt ctatatctgg cctgatgatt actccggaat ttggcagcaa cgttcgtctg 960
tgtgaagtgt ttacggatat gccgctgaac catgacaaac cgatctcctt cggcgttacc 1020
gaattctgta agacgtgcaa gaaatgcgcg gaagcgtgtg cgccgcaggc gatttcctat 1080
gaagacccga ccattgatgg cccgcgtggc cagatgcaga actccggcat caaacgctgg 1140
tatgttgatc cggtaaaatg tctggaattc atgtcccgcg ataatgttgg caattgctgc 1200
ggcgcgtgca ttgcggcgtg cccgtttacc aaaccggaag cgtggcatca caccctgatt 1260
cgctccctgg ttggcgcgcc ggttattacg ccgtttatga aagatatgga tgatatcttt 1320
ggctatggca aactgaatga tgagaaagcc atcgccgatt ggtggaaata g 1371

<210> SEQ ID NO 15
<211> LENGTH: 1371
<212> TYPE: DNA
<213> ORGANISM: Artificial Sequence
<220> FEATURE:
<223> OTHER INFORMATION: Synthetic cfrA R305Q

<400> SEQUENCE: 15
atggacaaag agaaatccaa caacgacaaa ccggcgacca agatcaaccg ccgccagttc 60
ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatcg cgcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720

```
ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840

gccgttccga ttggttctga cagcgccctg gccattccga ttgcgattca ggcgggtctg    900

ggcgaatatt ctcaatctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 16
<211> LENGTH: 1371
<212> TYPE: DNA
<213> ORGANISM: Artificial Sequence
<220> FEATURE:
<223> OTHER INFORMATION: Synthetic cfrA R305Q

<400> SEQUENCE: 16

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120

ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420

aacaagggtt tcttcgagtg gcacccgaaa gtggctgaac tgaacttcaa atggggcgac    480

ccagaacgta acatccacag cccaggtgtc aaatccgctg aagaaggtac catggctgtg    540

aagaagatcg cgcgtttctt cggtgctgct aaagcgggta tcgctccatt cgacaaacgt    600

tgggtcttca ccgaaaccta cgccttcgtg aagaccccag aaggtgaatc tctgaaattc    660

atcccgccgg acttcggctt cgaaccgaaa cacgttatca gcatgatcat cccgcagagc    720

ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840

gccgttccga ttggttctga cagcgccctg gccattccga ttgcgattca ggcgggtctg    900

ggcgaatatt ctcagtctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 17
<211> LENGTH: 1371
<212> TYPE: DNA
<213> ORGANISM: Artificial Sequence
<220> FEATURE:
<223> OTHER INFORMATION: Synthetic cfrA R305E

<400> SEQUENCE: 17

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120

ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420

aacaagggtt tcttcgagtg gcacccgaaa gtggctgaac tgaacttcaa atggggcgac    480

ccagaacgta acatccacag cccaggtgtc aaatccgctg aagaaggtac catggctgtg    540

aagaagatcg cgcgtttctt cggtgctgct aaagcgggta tcgctccatt cgacaaacgt    600

tgggtcttca ccgaaaccta cgccttcgtg aagaccccag aaggtgaatc tctgaaattc    660

atcccgccgg acttcggctt cgaaccgaaa cacgttatca gcatgatcat cccgcagagc    720

ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840

gccgttccga ttggttctga cagcgccctg gccattccga ttgcgattca ggcgggtctg    900

ggcgaatatt ctgaatctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 18
<211> LENGTH: 1371
<212> TYPE: DNA
<213> ORGANISM: Artificial Sequence
<220> FEATURE:
<223> OTHER INFORMATION: Synthetic cfrA R305E

<400> SEQUENCE: 18

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120

ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420
```

-continued

```
aacaagggtt tcttcgagtg gcacccgaaa gtggctgaac tgaacttcaa atggggcgac    480
ccagaacgta acatccacag cccaggtgtc aaatccgctg aagaaggtac catggctgtg    540
aagaagatcg cgcgtttctt cggtgctgct aaagcgggta tcgctccatt cgacaaacgt    600
tgggtcttca ccgaaaccta cgccttcgtg aagaccccag aaggtgaatc tctgaaattc    660
atcccgccgg acttcggctt cgaaccgaaa cacgttatca gcatgatcat cccgcagagc    720
ccggaaggtg tcaaatgcga cccgagcttt ctgggttcta ccgaatacgg tctgtcttgt    780
gctcaaatcg gttacgccgc cttcggtctg tctatgttca tcaaagacct gggctaccac    840
gccgttccga ttggttctga cagcgccctg gccattccga ttgcgattca ggcgggtctg    900
ggcgaatatt ctgagtctgg cctgatgatt actccggaat ttggcagcaa cgttcgtctg    960
tgtgaagtgt ttacggatat gccgctgaac catgacaaac cgatctcctt cggcgttacc   1020
gaattctgta agacgtgcaa gaaatgcgcg gaagcgtgtg cgccgcaggc gatttcctat   1080
gaagacccga ccattgatgg cccgcgtggc cagatgcaga actccggcat caaacgctgg   1140
tatgttgatc cggtaaaatg tctggaattc atgtcccgcg ataatgttgg caattgctgc   1200
ggcgcgtgca ttgcggcgtg cccgtttacc aaaccggaag cgtggcatca caccctgatt   1260
cgctccctgg ttggcgcgcc ggttattacg ccgtttatga aagatatgga tgatatcttt   1320
ggctatggca aactgaatga tgagaaagcc atcgccgatt ggtggaaata g            1371
```

```
<210> SEQ ID NO 19
<211> LENGTH: 1371
<212> TYPE: DNA
<213> ORGANISM: Artificial Sequence
<220> FEATURE:
<223> OTHER INFORMATION: Synthetic cfrA R305S

<400> SEQUENCE: 19

atggacaaag agaaatccaa caacgacaaa ccggcgacca agatcaaccg ccgccagttc      60
ctgaaattcg gcgcaggtgc atctagcggt atcgctatcg caactgcagc aactgcactg    120
ggtggcaaat ccctgatcga tcctaaacag gtgtacgcag gtactgtgaa agagctggac    180
gagctgccgt tcaacatccc tgcagactac aaaccgttca ctaaccagcg taacatctac    240
ggccaggcag tactgggtgt acctgagcct ctggcactgg tagaacgctt tgacgaagta    300
cgttggaacg gttggcaaac tgacggttct ccaggtctga ccgttctgga tggtgcagct    360
gcgcgtgcta gctttgctgt tgattattac ttcaacggcg agaactctgc ttgccgtgct    420
aacaagggtt tcttcgagtg gcacccgaaa gtggctgaac tgaacttcaa atggggcgac    480
ccagaacgta acatccacag cccaggtgtc aaatccgctg aagaaggtac catggctgtg    540
aagaagatcg cgcgtttctt cggtgctgct aaagcgggta tcgctccatt cgacaaacgt    600
tgggtcttca ccgaaaccta cgccttcgtg aagaccccag aaggtgaatc tctgaaattc    660
atcccgccgg acttcggctt cgaaccgaaa cacgttatca gcatgatcat cccgcagagc    720
ccggaaggtg tcaaatgcga cccgagcttt ctgggttcta ccgaatacgg tctgtcttgt    780
gctcaaatcg gttacgccgc cttcggtctg tctatgttca tcaaagacct gggctaccac    840
gccgttccga ttggttctga cagcgccctg gccattccga ttgcgattca ggcgggtctg    900
ggcgaatatt ctagttctgg cctgatgatt actccggaat ttggcagcaa cgttcgtctg    960
tgtgaagtgt ttacggatat gccgctgaac catgacaaac cgatctcctt cggcgttacc   1020
gaattctgta agacgtgcaa gaaatgcgcg gaagcgtgtg cgccgcaggc gatttcctat   1080
gaagacccga ccattgatgg cccgcgtggc cagatgcaga actccggcat caaacgctgg   1140
```

-continued

```
tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 20
<211> LENGTH: 1371
<212> TYPE: DNA
<213> ORGANISM: Artificial Sequence
<220> FEATURE:
<223> OTHER INFORMATION: Synthetic cfrA R305S

<400> SEQUENCE: 20

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120

ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420

aacaagggtt tcttcgagtg gcacccgaaa gtggctgaac tgaacttcaa atggggcgac    480

ccagaacgta acatccacag cccaggtgtc aaatccgctg aagaaggtac catggctgtg    540

aagaagatcg cgcgtttctt cggtgctgct aaagcgggta tcgctccatt cgacaaacgt    600

tgggtcttca ccgaaaccta cgccttcgtg aagaccccag aaggtgaatc tctgaaattc    660

atcccgccgg acttcggctt cgaaccgaaa cacgttatca gcatgatcat cccgcagagc    720

ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840

gccgttccga ttggttctga cagcgccctg gccattccga ttgcgattca ggcgggtctg    900

ggcgaatatt ctagctctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 21
<211> LENGTH: 1371
<212> TYPE: DNA
<213> ORGANISM: Artificial Sequence
<220> FEATURE:
<223> OTHER INFORMATION: Synthetic cfrA R305S

<400> SEQUENCE: 21

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120
```

-continued

```
ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420

aacaagggtt tcttcgagtg gcacccgaaa gtggctgaac tgaacttcaa atggggcgac    480

ccagaacgta acatccacag cccaggtgtc aaatccgctg aagaaggtac catggctgtg    540

aagaagatcg cgcgtttctt cggtgctgct aaagcgggta tcgctccatt cgacaaacgt    600

tgggtcttca ccgaaaccta cgccttcgtg aagaccccag aaggtgaatc tctgaaattc    660

atcccgccgg acttcggctt cgaaccgaaa cacgttatca gcatgatcat cccgcagagc    720

ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840

gccgttccga ttggttctga cagcgccctg gccattccga ttgcgattca ggcgggtctg    900

ggcgaatatt cttcttctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 22
<211> LENGTH: 1371
<212> TYPE: DNA
<213> ORGANISM: Artificial Sequence
<220> FEATURE:
<223> OTHER INFORMATION: Synthetic cfrA R305S

<400> SEQUENCE: 22

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120

ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420

aacaagggtt tcttcgagtg gcacccgaaa gtggctgaac tgaacttcaa atggggcgac    480

ccagaacgta acatccacag cccaggtgtc aaatccgctg aagaaggtac catggctgtg    540

aagaagatcg cgcgtttctt cggtgctgct aaagcgggta tcgctccatt cgacaaacgt    600

tgggtcttca ccgaaaccta cgccttcgtg aagaccccag aaggtgaatc tctgaaattc    660

atcccgccgg acttcggctt cgaaccgaaa cacgttatca gcatgatcat cccgcagagc    720

ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840
```

-continued

```
gccgttccga ttggttctga cagcgccctg gccattccga ttgcgattca ggcgggtctg    900

ggcgaatatt cttcctctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 23
<211> LENGTH: 1371
<212> TYPE: DNA
<213> ORGANISM: Artificial Sequence
<220> FEATURE:
<223> OTHER INFORMATION: Synthetic cfrA R305S

<400> SEQUENCE: 23

```
atggacaaag agaaatccaa caacgacaaa ccggcgacca agatcaaccg ccgccagttc     60

ctgaaattcg gcgcaggtgc atctagcggt atcgctatcg caactgcagc aactgcactg    120

ggtggcaaat ccctgatcga tcctaaacag gtgtacgcag gtactgtgaa agagctggac    180

gagctgccgt tcaacatccc tgcagactac aaaccgttca ctaaccagcg taacatctac    240

ggccaggcag tactgggtgt acctgagcct ctggcactgg tagaacgctt tgacgaagta    300

cgttggaacg gttggcaaac tgacggttct ccaggtctga ccgttctgga tggtgcagct    360

gcgcgtgcta gctttgctgt tgattattac ttcaacggcg agaactctgc ttgccgtgct    420

aacaagggtt tcttcgagtg gcacccgaaa gtggctgaac tgaacttcaa atggggcgac    480

ccagaacgta acatccacag cccaggtgtc aaatccgctg aagaaggtac catggctgtg    540

aagaagatcg cgcgtttctt cggtgctgct aaagcgggta tcgctccatt cgacaaacgt    600

tgggtcttca ccgaaaccta cgccttcgtg aagaccccag aaggtgaatc tctgaaattc    660

atcccgccgg acttcggctt cgaaccgaaa cacgttatca gcatgatcat cccgcagagc    720

ccggaaggtg tcaaatgcga cccgagcttt ctgggttcta ccgaatacgg tctgtcttgt    780

gctcaaatcg gttacgccgc cttcggtctg tctatgttca tcaaagacct gggctaccac    840

gccgttccga ttggttctga cagcgccctg gccattccga ttgcgattca ggcgggtctg    900

ggcgaatatt cttcatctgg cctgatgatt actccggaat ttggcagcaa cgttcgtctg    960

tgtgaagtgt ttacggatat gccgctgaac catgacaaac cgatctcctt cggcgttacc   1020

gaattctgta agacgtgcaa gaaatgcgcg gaagcgtgtg cgccgcaggc gatttcctat   1080

gaagacccga ccattgatgg cccgcgtggc cagatgcaga actccggcat caaacgctgg   1140

tatgttgatc cggtaaaatg tctggaattc atgtcccgcg ataatgttgg caattgctgc   1200

ggcgcgtgca ttgcggcgtg cccgtttacc aaaccggaag cgtggcatca caccctgatt   1260

cgctccctgg ttggcgcgcc ggttattacg ccgtttatga aagatatgga tgatatcttt   1320

ggctatggca aactgaatga tgagaaagcc atcgccgatt ggtggaaata g            1371
```

<210> SEQ ID NO 24
<211> LENGTH: 1371
<212> TYPE: DNA

<213> ORGANISM: Artificial Sequence
<220> FEATURE:
<223> OTHER INFORMATION: Synthetic cfrA R305S

<400> SEQUENCE: 24

```
atggacaaag agaaatccaa caacgacaaa ccggcgacca agatcaaccg ccgccagttc      60

ctgaaattcg gcgcaggtgc atctagcggt atcgctatcg caactgcagc aactgcactg     120

ggtggcaaat ccctgatcga tcctaaacag gtgtacgcag gtactgtgaa agagctggac     180

gagctgccgt tcaacatccc tgcagactac aaaccgttca ctaaccagcg taacatctac     240

ggccaggcag tactgggtgt acctgagcct ctggcactgg tagaacgctt tgacgaagta     300

cgttggaacg gttggcaaac tgacggttct ccaggtctga ccgttctgga tggtgcagct     360

gcgcgtgcta gctttgctgt tgattattac ttcaacggcg agaactctgc ttgccgtgct     420

aacaagggtt tcttcgagtg gcacccgaaa gtggctgaac tgaacttcaa atggggcgac     480

ccagaacgta acatccacag cccaggtgtc aaatccgctg aagaaggtac catggctgtg     540

aagaagatcg cgcgtttctt cggtgctgct aaagcgggta tcgctccatt cgacaaacgt     600

tgggtcttca ccgaaaccta cgccttcgtg aagaccccag aaggtgaatc tctgaaattc     660

atcccgccgg acttcggctt cgaaccgaaa cacgttatca gcatgatcat cccgcagagc     720

ccggaaggtg tcaaatgcga cccgagcttt ctgggttcta ccgaatacgg tctgtcttgt     780

gctcaaatcg gttacgccgc cttcggtctg tctatgttca tcaaagacct gggctaccac     840

gccgttccga ttggttctga cagcgccctg gccattccga ttgcgattca ggcgggtctg     900

ggcgaatatt cttcgtctgg cctgatgatt actccggaat ttggcagcaa cgttcgtctg     960

tgtgaagtgt ttacggatat gccgctgaac catgacaaac cgatctcctt cggcgttacc    1020

gaattctgta agacgtgcaa gaaatgcgcg gaagcgtgtg cgccgcaggc gatttcctat    1080

gaagacccga ccattgatgg cccgcgtggc cagatgcaga actccggcat caaacgctgg    1140

tatgttgatc cggtaaaatg tctggaattc atgtcccgcg ataatgttgg caattgctgc    1200

ggcgcgtgca ttgcggcgtg cccgtttacc aaaccggaag cgtggcatca caccctgatt    1260

cgctccctgg ttggcgcgcc ggttattacg ccgtttatga aagatatgga tgatatcttt    1320

ggctatggca aactgaatga tgagaaagcc atcgccgatt ggtggaaata g             1371
```

<210> SEQ ID NO 25
<211> LENGTH: 456
<212> TYPE: PRT
<213> ORGANISM: Artificial Sequence
<220> FEATURE:
<223> OTHER INFORMATION: Synthetic cfrA R305Q

<400> SEQUENCE: 25

```
Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95
```

-continued

```
Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Tyr His Ala Val Pro Ile Gly Ser Asp Ser
        275                 280                 285

Ala Leu Ala Ile Pro Ile Ala Ile Gln Ala Gly Leu Gly Glu Tyr Ser
    290                 295                 300

Gln Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro
        355                 360                 365

Arg Gly Gln Met Gln Asn Ser Gly Ile Lys Arg Trp Tyr Val Asp Pro
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
    450                 455
```

<210> SEQ ID NO 26
<211> LENGTH: 456
<212> TYPE: PRT
<213> ORGANISM: Artificial Sequence
<220> FEATURE:
<223> OTHER INFORMATION: Synthetic cfrA R305E

<400> SEQUENCE: 26

-continued

```
Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Tyr His Ala Val Pro Ile Gly Ser Asp Ser
        275                 280                 285

Ala Leu Ala Ile Pro Ile Ala Ile Gln Ala Gly Leu Gly Glu Tyr Ser
    290                 295                 300

Glu Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro
        355                 360                 365

Arg Gly Gln Met Gln Asn Ser Gly Ile Lys Arg Trp Tyr Val Asp Pro
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415
```

-continued

```
His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
    450                 455


<210> SEQ ID NO 27
<211> LENGTH: 456
<212> TYPE: PRT
<213> ORGANISM: Artificial Sequence
<220> FEATURE:
<223> OTHER INFORMATION: Synthetic cfrA R305S

<400> SEQUENCE: 27

Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Tyr His Ala Val Pro Ile Gly Ser Asp Ser
        275                 280                 285

Ala Leu Ala Ile Pro Ile Ala Ile Gln Ala Gly Leu Gly Glu Tyr Ser
    290                 295                 300

Ser Ser Gly Leu Met Ile Thr Pro Glu Phe Gly Ser Asn Val Arg Leu
305                 310                 315                 320
```

-continued

```
Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro
        355                 360                 365

Arg Gly Gln Met Gln Asn Ser Gly Ile Lys Arg Trp Tyr Val Asp Pro
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
    450                 455
```

<210> SEQ ID NO 28
<211> LENGTH: 44
<212> TYPE: DNA
<213> ORGANISM: Artificial Sequence
<220> FEATURE:
<223> OTHER INFORMATION: Synthetic CfrA F-primer

<400> SEQUENCE: 28
atcgagggaa ggatttcaga attcatggac aaagagaaat ccaa 44

<210> SEQ ID NO 29
<211> LENGTH: 44
<212> TYPE: DNA
<213> ORGANISM: Artificial Sequence
<220> FEATURE:
<223> OTHER INFORMATION: Synthetic CfrA R-primer

<400> SEQUENCE: 29
gtcgactcta gaggatccga attcttacta tttccaccaa tcgg 44

<210> SEQ ID NO 30
<211> LENGTH: 18
<212> TYPE: DNA
<213> ORGANISM: Artificial Sequence
<220> FEATURE:
<223> OTHER INFORMATION: Synthetic 305 PMR primer

<400> SEQUENCE: 30
agaatattcg cccagacc 18

<210> SEQ ID NO 31
<211> LENGTH: 37
<212> TYPE: DNA
<213> ORGANISM: Artificial Sequence
<220> FEATURE:
<223> OTHER INFORMATION: Synthetic Phe305 primer

<400> SEQUENCE: 31
ctgggcgaat attctttttc tggcctgatg attactc 37

<210> SEQ ID NO 32
<211> LENGTH: 37
<212> TYPE: DNA

<213> ORGANISM: Artificial Sequence
<220> FEATURE:
<223> OTHER INFORMATION: Synthetic Val305 primer

<400> SEQUENCE: 32
ctgggcgaat attctgtgtc tggcctgatg attactc 37

<210> SEQ ID NO 33
<211> LENGTH: 37
<212> TYPE: DNA
<213> ORGANISM: Artificial Sequence
<220> FEATURE:
<223> OTHER INFORMATION: Synthetic Ala305 primer

<400> SEQUENCE: 33
ctgggcgaat attctgcgtc tggcctgatg attactc 37

<210> SEQ ID NO 34
<211> LENGTH: 37
<212> TYPE: DNA
<213> ORGANISM: Artificial Sequence
<220> FEATURE:
<223> OTHER INFORMATION: Synthetic Asn305 primer

<400> SEQUENCE: 34
ctgggcgaat attctaactc tggcctgatg attactc 37

<210> SEQ ID NO 35
<211> LENGTH: 37
<212> TYPE: DNA
<213> ORGANISM: Artificial Sequence
<220> FEATURE:
<223> OTHER INFORMATION: Synthetic Cys305 primer

<400> SEQUENCE: 35
ctgggcgaat attcttgctc tggcctgatg attactc 37

<210> SEQ ID NO 36
<211> LENGTH: 37
<212> TYPE: DNA
<213> ORGANISM: Artificial Sequence
<220> FEATURE:
<223> OTHER INFORMATION: Synthetic Leu305 primer

<400> SEQUENCE: 36
ctgggcgaat attctctgtc tggcctgatg attactc 37

<210> SEQ ID NO 37
<211> LENGTH: 37
<212> TYPE: DNA
<213> ORGANISM: Artificial Sequence
<220> FEATURE:
<223> OTHER INFORMATION: Synthetic Gly305 primer

<400> SEQUENCE: 37
ctgggcgaat attctggctc tggcctgatg attactc 37

<210> SEQ ID NO 38
<211> LENGTH: 37
<212> TYPE: DNA
<213> ORGANISM: Artificial Sequence
<220> FEATURE:
<223> OTHER INFORMATION: Synthetic Tyr305 primer

<400> SEQUENCE: 38
ctgggcgaat attcttattc tggcctgatg attactc 37

<210> SEQ ID NO 39
<211> LENGTH: 37
<212> TYPE: DNA
<213> ORGANISM: Artificial Sequence
<220> FEATURE:
<223> OTHER INFORMATION: Synthetic Lys305 primer

<400> SEQUENCE: 39
ctgggcgaat attctaaatc tggcctgatg attactc 37

<210> SEQ ID NO 40
<211> LENGTH: 37
<212> TYPE: DNA
<213> ORGANISM: Artificial Sequence
<220> FEATURE:
<223> OTHER INFORMATION: Synthetic Trp305 primer

<400> SEQUENCE: 40
ctgggcgaat attcttggtc tggcctgatg attactc 37

<210> SEQ ID NO 41
<211> LENGTH: 37
<212> TYPE: DNA
<213> ORGANISM: Artificial Sequence
<220> FEATURE:
<223> OTHER INFORMATION: Synthetic Ile305 primer

<400> SEQUENCE: 41
ctgggcgaat attctatttc tggcctgatg attactc 37

<210> SEQ ID NO 42
<211> LENGTH: 37
<212> TYPE: DNA
<213> ORGANISM: Artificial Sequence
<220> FEATURE:
<223> OTHER INFORMATION: Synthetic Pro305 primer

<400> SEQUENCE: 42
ctgggcgaat attctccgtc tggcctgatg attactc 37

<210> SEQ ID NO 43
<211> LENGTH: 37
<212> TYPE: DNA
<213> ORGANISM: Artificial Sequence
<220> FEATURE:
<223> OTHER INFORMATION: Synthetic His305 primer

<400> SEQUENCE: 43
ctgggcgaat attctcattc tggcctgatg attactc 37

<210> SEQ ID NO 44
<211> LENGTH: 37
<212> TYPE: DNA
<213> ORGANISM: Artificial Sequence
<220> FEATURE:
<223> OTHER INFORMATION: Synthetic Asp305 primer

<400> SEQUENCE: 44
ctgggcgaat attctgattc tggcctgatg attactc 37

<210> SEQ ID NO 45
<211> LENGTH: 37
<212> TYPE: DNA
<213> ORGANISM: Artificial Sequence
<220> FEATURE:

-continued

<223> OTHER INFORMATION: Synthetic Met305 primer

<400> SEQUENCE: 45
ctgggcgaat attctatgtc tggcctgatg attactc 37

<210> SEQ ID NO 46
<211> LENGTH: 37
<212> TYPE: DNA
<213> ORGANISM: Artificial Sequence
<220> FEATURE:
<223> OTHER INFORMATION: Synthetic Thr305 primer

<400> SEQUENCE: 46
ctgggcgaat attctacctc tggcctgatg attactc 37

<210> SEQ ID NO 47
<211> LENGTH: 37
<212> TYPE: DNA
<213> ORGANISM: Artificial Sequence
<220> FEATURE:
<223> OTHER INFORMATION: Synthetic Gln305 primer

<400> SEQUENCE: 47
ctgggcgaat attctcagtc tggcctgatg attactc 37

<210> SEQ ID NO 48
<211> LENGTH: 37
<212> TYPE: DNA
<213> ORGANISM: Artificial Sequence
<220> FEATURE:
<223> OTHER INFORMATION: Synthetic Glu305 primer

<400> SEQUENCE: 48
ctgggcgaat attctgaatc tggcctgatg attactc 37

<210> SEQ ID NO 49
<211> LENGTH: 37
<212> TYPE: DNA
<213> ORGANISM: Artificial Sequence
<220> FEATURE:
<223> OTHER INFORMATION: Synthetic Ser305 primer

<400> SEQUENCE: 49
ctgggcgaat attctagctc tggcctgatg attactc 37

<210> SEQ ID NO 50
<211> LENGTH: 18
<212> TYPE: DNA
<213> ORGANISM: Artificial Sequence
<220> FEATURE:
<223> OTHER INFORMATION: Synthetic 184 PMR primer

<400> SEQUENCE: 50
gatcttcttc acagccat 18

<210> SEQ ID NO 51
<211> LENGTH: 37
<212> TYPE: DNA
<213> ORGANISM: Artificial Sequence
<220> FEATURE:
<223> OTHER INFORMATION: Synthetic Phe184 primer

<400> SEQUENCE: 51
atggctgtga agaagatctt tcgtttcttc ggtgctg 37

<210> SEQ ID NO 52
<211> LENGTH: 37
<212> TYPE: DNA
<213> ORGANISM: Artificial Sequence
<220> FEATURE:
<223> OTHER INFORMATION: Synthetic Val184 primer

<400> SEQUENCE: 52
atggctgtga agaagatcgt gcgtttcttc ggtgctg 37

<210> SEQ ID NO 53
<211> LENGTH: 37
<212> TYPE: DNA
<213> ORGANISM: Artificial Sequence
<220> FEATURE:
<223> OTHER INFORMATION: Synthetic Glu184 primer

<400> SEQUENCE: 53
atggctgtga agaagatcga acgtttcttc ggtgctg 37

<210> SEQ ID NO 54
<211> LENGTH: 37
<212> TYPE: DNA
<213> ORGANISM: Artificial Sequence
<220> FEATURE:
<223> OTHER INFORMATION: Synthetic Asn184 primer

<400> SEQUENCE: 54
atggctgtga agaagatcaa ccgtttcttc ggtgctg 37

<210> SEQ ID NO 55
<211> LENGTH: 37
<212> TYPE: DNA
<213> ORGANISM: Artificial Sequence
<220> FEATURE:
<223> OTHER INFORMATION: Synthetic Cys184 primer

<400> SEQUENCE: 55
atggctgtga agaagatctg ccgtttcttc ggtgctg 37

<210> SEQ ID NO 56
<211> LENGTH: 37
<212> TYPE: DNA
<213> ORGANISM: Artificial Sequence
<220> FEATURE:
<223> OTHER INFORMATION: Synthetic Leu184 primer

<400> SEQUENCE: 56
atggctgtga agaagatcct gcgtttcttc ggtgctg 37

<210> SEQ ID NO 57
<211> LENGTH: 37
<212> TYPE: DNA
<213> ORGANISM: Artificial Sequence
<220> FEATURE:
<223> OTHER INFORMATION: Synthetic Gly184 primer

<400> SEQUENCE: 57
atggctgtga agaagatcgg ccgtttcttc ggtgctg 37

<210> SEQ ID NO 58
<211> LENGTH: 37
<212> TYPE: DNA
<213> ORGANISM: Artificial Sequence
<220> FEATURE:
<223> OTHER INFORMATION: Synthetic Tyr184 primer

<400> SEQUENCE: 58
atggctgtga agaagatcta tcgtttcttc ggtgctg 37

<210> SEQ ID NO 59
<211> LENGTH: 37
<212> TYPE: DNA
<213> ORGANISM: Artificial Sequence
<220> FEATURE:
<223> OTHER INFORMATION: Synthetic Lys184 primer

<400> SEQUENCE: 59
atggctgtga agaagatcaa acgtttcttc ggtgctg 37

<210> SEQ ID NO 60
<211> LENGTH: 37
<212> TYPE: DNA
<213> ORGANISM: Artificial Sequence
<220> FEATURE:
<223> OTHER INFORMATION: Synthetic Trp184 primer

<400> SEQUENCE: 60
atggctgtga agaagatctg gcgtttcttc ggtgctg 37

<210> SEQ ID NO 61
<211> LENGTH: 37
<212> TYPE: DNA
<213> ORGANISM: Artificial Sequence
<220> FEATURE:
<223> OTHER INFORMATION: Synthetic Ile184 primer

<400> SEQUENCE: 61
atggctgtga agaagatcat tcgtttcttc ggtgctg 37

<210> SEQ ID NO 62
<211> LENGTH: 37
<212> TYPE: DNA
<213> ORGANISM: Artificial Sequence
<220> FEATURE:
<223> OTHER INFORMATION: Synthetic Pro184 primer

<400> SEQUENCE: 62
atggctgtga agaagatccc gcgtttcttc ggtgctg 37

<210> SEQ ID NO 63
<211> LENGTH: 37
<212> TYPE: DNA
<213> ORGANISM: Artificial Sequence
<220> FEATURE:
<223> OTHER INFORMATION: Synthetic His184 primer

<400> SEQUENCE: 63
atggctgtga agaagatcca tcgtttcttc ggtgctg 37

<210> SEQ ID NO 64
<211> LENGTH: 37
<212> TYPE: DNA
<213> ORGANISM: Artificial Sequence
<220> FEATURE:
<223> OTHER INFORMATION: Synthetic Asp184 primer

<400> SEQUENCE: 64
atggctgtga agaagatcga tcgtttcttc ggtgctg 37

<210> SEQ ID NO 65
<211> LENGTH: 37

<212> TYPE: DNA
<213> ORGANISM: Artificial Sequence
<220> FEATURE:
<223> OTHER INFORMATION: Synthetic Met184 primer

<400> SEQUENCE: 65
atggctgtga agaagatcat gcgtttcttc ggtgctg 37

<210> SEQ ID NO 66
<211> LENGTH: 37
<212> TYPE: DNA
<213> ORGANISM: Artificial Sequence
<220> FEATURE:
<223> OTHER INFORMATION: Synthetic Thr184 primer

<400> SEQUENCE: 66
atggctgtga agaagatcac ccgtttcttc ggtgctg 37

<210> SEQ ID NO 67
<211> LENGTH: 37
<212> TYPE: DNA
<213> ORGANISM: Artificial Sequence
<220> FEATURE:
<223> OTHER INFORMATION: Synthetic Gln184 primer

<400> SEQUENCE: 67
atggctgtga agaagatcca gcgtttcttc ggtgctg 37

<210> SEQ ID NO 68
<211> LENGTH: 37
<212> TYPE: DNA
<213> ORGANISM: Artificial Sequence
<220> FEATURE:
<223> OTHER INFORMATION: Synthetic Arg184 primer

<400> SEQUENCE: 68
atggctgtga agaagatccg tcgtttcttc ggtgctg 37

<210> SEQ ID NO 69
<211> LENGTH: 37
<212> TYPE: DNA
<213> ORGANISM: Artificial Sequence
<220> FEATURE:
<223> OTHER INFORMATION: Synthetic Ser184 primer

<400> SEQUENCE: 69
atggctgtga agaagatcag ccgtttcttc ggtgctg 37

<210> SEQ ID NO 70
<211> LENGTH: 16
<212> TYPE: DNA
<213> ORGANISM: Artificial Sequence
<220> FEATURE:
<223> OTHER INFORMATION: Synthetic 279 PMR primer

<400> SEQUENCE: 70
gcccaggtct ttgatg 16

<210> SEQ ID NO 71
<211> LENGTH: 34
<212> TYPE: DNA
<213> ORGANISM: Artificial Sequence
<220> FEATURE:
<223> OTHER INFORMATION: Synthetic Phe279 primer

<400> SEQUENCE: 71
catcaaagac ctgggctttc acgccgttcc gatt 34

<210> SEQ ID NO 72
<211> LENGTH: 34
<212> TYPE: DNA
<213> ORGANISM: Artificial Sequence
<220> FEATURE:
<223> OTHER INFORMATION: Synthetic Val279 primer

<400> SEQUENCE: 72
catcaaagac ctgggcgtgc acgccgttcc gatt 34

<210> SEQ ID NO 73
<211> LENGTH: 34
<212> TYPE: DNA
<213> ORGANISM: Artificial Sequence
<220> FEATURE:
<223> OTHER INFORMATION: Synthetic Ala279 primer

<400> SEQUENCE: 73
catcaaagac ctgggcgcgc acgccgttcc gatt 34

<210> SEQ ID NO 74
<211> LENGTH: 34
<212> TYPE: DNA
<213> ORGANISM: Artificial Sequence
<220> FEATURE:
<223> OTHER INFORMATION: Synthetic Asn279 primer

<400> SEQUENCE: 74
catcaaagac ctgggcaacc acgccgttcc gatt 34

<210> SEQ ID NO 75
<211> LENGTH: 34
<212> TYPE: DNA
<213> ORGANISM: Artificial Sequence
<220> FEATURE:
<223> OTHER INFORMATION: Synthetic Cys279 primer

<400> SEQUENCE: 75
catcaaagac ctgggctgcc acgccgttcc gatt 34

<210> SEQ ID NO 76
<211> LENGTH: 34
<212> TYPE: DNA
<213> ORGANISM: Artificial Sequence
<220> FEATURE:
<223> OTHER INFORMATION: Synthetic Leu279 primer

<400> SEQUENCE: 76
catcaaagac ctgggcctgc acgccgttcc gatt 34

<210> SEQ ID NO 77
<211> LENGTH: 34
<212> TYPE: DNA
<213> ORGANISM: Artificial Sequence
<220> FEATURE:
<223> OTHER INFORMATION: Synthetic Gly279 primer

<400> SEQUENCE: 77
catcaaagac ctgggcggcc acgccgttcc gatt 34

<210> SEQ ID NO 78
<211> LENGTH: 34
<212> TYPE: DNA
<213> ORGANISM: Artificial Sequence

```
<220> FEATURE:
<223> OTHER INFORMATION: Synthetic Tyr279 primer

<400> SEQUENCE: 78

catcaaagac ctgggctatc acgccgttcc gatt                              34


<210> SEQ ID NO 79
<211> LENGTH: 34
<212> TYPE: DNA
<213> ORGANISM: Artificial Sequence
<220> FEATURE:
<223> OTHER INFORMATION: Synthetic Lys279 primer

<400> SEQUENCE: 79

catcaaagac ctgggcaaac acgccgttcc gatt                              34


<210> SEQ ID NO 80
<211> LENGTH: 34
<212> TYPE: DNA
<213> ORGANISM: Artificial Sequence
<220> FEATURE:
<223> OTHER INFORMATION: Synthetic Trp279 primer

<400> SEQUENCE: 80

catcaaagac ctgggctggc acgccgttcc gatt                              34


<210> SEQ ID NO 81
<211> LENGTH: 34
<212> TYPE: DNA
<213> ORGANISM: Artificial Sequence
<220> FEATURE:
<223> OTHER INFORMATION: Synthetic Ile279 primer

<400> SEQUENCE: 81

catcaaagac ctgggcattc acgccgttcc gatt                              34


<210> SEQ ID NO 82
<211> LENGTH: 34
<212> TYPE: DNA
<213> ORGANISM: Artificial Sequence
<220> FEATURE:
<223> OTHER INFORMATION: Synthetic Pro279 primer

<400> SEQUENCE: 82

catcaaagac ctgggcccgc acgccgttcc gatt                              34


<210> SEQ ID NO 83
<211> LENGTH: 34
<212> TYPE: DNA
<213> ORGANISM: Artificial Sequence
<220> FEATURE:
<223> OTHER INFORMATION: Synthetic His279 primer

<400> SEQUENCE: 83

catcaaagac ctgggccatc acgccgttcc gatt                              34


<210> SEQ ID NO 84
<211> LENGTH: 34
<212> TYPE: DNA
<213> ORGANISM: Artificial Sequence
<220> FEATURE:
<223> OTHER INFORMATION: Synthetic Asp279 primer

<400> SEQUENCE: 84

catcaaagac ctgggcgatc acgccgttcc gatt                              34
```

<210> SEQ ID NO 85
<211> LENGTH: 34
<212> TYPE: DNA
<213> ORGANISM: Artificial Sequence
<220> FEATURE:
<223> OTHER INFORMATION: Synthetic Met279 primer

<400> SEQUENCE: 85
catcaaagac ctgggcatgc acgccgttcc gatt 34

<210> SEQ ID NO 86
<211> LENGTH: 34
<212> TYPE: DNA
<213> ORGANISM: Artificial Sequence
<220> FEATURE:
<223> OTHER INFORMATION: Synthetic Thr279 primer

<400> SEQUENCE: 86
catcaaagac ctgggcaccc acgccgttcc gatt 34

<210> SEQ ID NO 87
<211> LENGTH: 34
<212> TYPE: DNA
<213> ORGANISM: Artificial Sequence
<220> FEATURE:
<223> OTHER INFORMATION: Synthetic Gln279 primer

<400> SEQUENCE: 87
catcaaagac ctgggccagc acgccgttcc gatt 34

<210> SEQ ID NO 88
<211> LENGTH: 34
<212> TYPE: DNA
<213> ORGANISM: Artificial Sequence
<220> FEATURE:
<223> OTHER INFORMATION: Synthetic Glu279 primer

<400> SEQUENCE: 88
catcaaagac ctgggcgaac acgccgttcc gatt 34

<210> SEQ ID NO 89
<211> LENGTH: 34
<212> TYPE: DNA
<213> ORGANISM: Artificial Sequence
<220> FEATURE:
<223> OTHER INFORMATION: Synthetic Ser279 primer

<400> SEQUENCE: 89
catcaaagac ctgggcagcc acgccgttcc gatt 34

<210> SEQ ID NO 90
<211> LENGTH: 15
<212> TYPE: DNA
<213> ORGANISM: Artificial Sequence
<220> FEATURE:
<223> OTHER INFORMATION: Synthetic 302 PMR primer

<400> SEQUENCE: 90
gcccagaccc gcctg 15

<210> SEQ ID NO 91
<211> LENGTH: 36
<212> TYPE: DNA
<213> ORGANISM: Artificial Sequence
<220> FEATURE:
<223> OTHER INFORMATION: Synthetic Phe302 primer

<400> SEQUENCE: 91
caggcgggtc tgggctttta ttctatttct ggcctg 36

<210> SEQ ID NO 92
<211> LENGTH: 36
<212> TYPE: DNA
<213> ORGANISM: Artificial Sequence
<220> FEATURE:
<223> OTHER INFORMATION: Synthetic Val302 primer

<400> SEQUENCE: 92
caggcgggtc tgggcgtgta ttctatttct ggcctg 36

<210> SEQ ID NO 93
<211> LENGTH: 36
<212> TYPE: DNA
<213> ORGANISM: Artificial Sequence
<220> FEATURE:
<223> OTHER INFORMATION: Synthetic Ala302 primer

<400> SEQUENCE: 93
caggcgggtc tgggcgcgta ttctatttct ggcctg 36

<210> SEQ ID NO 94
<211> LENGTH: 36
<212> TYPE: DNA
<213> ORGANISM: Artificial Sequence
<220> FEATURE:
<223> OTHER INFORMATION: Synthetic Asn302 primer

<400> SEQUENCE: 94
caggcgggtc tgggcaacta ttctatttct ggcctg 36

<210> SEQ ID NO 95
<211> LENGTH: 36
<212> TYPE: DNA
<213> ORGANISM: Artificial Sequence
<220> FEATURE:
<223> OTHER INFORMATION: Synthetic Cys302 primer

<400> SEQUENCE: 95
caggcgggtc tgggctgcta ttctatttct ggcctg 36

<210> SEQ ID NO 96
<211> LENGTH: 36
<212> TYPE: DNA
<213> ORGANISM: Artificial Sequence
<220> FEATURE:
<223> OTHER INFORMATION: Synthetic Leu302 primer

<400> SEQUENCE: 96
caggcgggtc tgggcctgta ttctatttct ggcctg 36

<210> SEQ ID NO 97
<211> LENGTH: 36
<212> TYPE: DNA
<213> ORGANISM: Artificial Sequence
<220> FEATURE:
<223> OTHER INFORMATION: Synthetic Gly302 primer

<400> SEQUENCE: 97
caggcgggtc tgggcggcta ttctatttct ggcctg 36

<210> SEQ ID NO 98

<211> LENGTH: 36
<212> TYPE: DNA
<213> ORGANISM: Artificial Sequence
<220> FEATURE:
<223> OTHER INFORMATION: Synthetic Tyr302 primer

<400> SEQUENCE: 98
caggcgggtc tgggctatta ttctatttct ggcctg 36

<210> SEQ ID NO 99
<211> LENGTH: 36
<212> TYPE: DNA
<213> ORGANISM: Artificial Sequence
<220> FEATURE:
<223> OTHER INFORMATION: Synthetic Lys302 primer

<400> SEQUENCE: 99
caggcgggtc tgggcaaata ttctatttct ggcctg 36

<210> SEQ ID NO 100
<211> LENGTH: 36
<212> TYPE: DNA
<213> ORGANISM: Artificial Sequence
<220> FEATURE:
<223> OTHER INFORMATION: Synthetic Trp302 primer

<400> SEQUENCE: 100
caggcgggtc tgggctggta ttctatttct ggcctg 36

<210> SEQ ID NO 101
<211> LENGTH: 36
<212> TYPE: DNA
<213> ORGANISM: Artificial Sequence
<220> FEATURE:
<223> OTHER INFORMATION: Synthetic Ile302 primer

<400> SEQUENCE: 101
caggcgggtc tgggcattta ttctatttct ggcctg 36

<210> SEQ ID NO 102
<211> LENGTH: 36
<212> TYPE: DNA
<213> ORGANISM: Artificial Sequence
<220> FEATURE:
<223> OTHER INFORMATION: Synthetic Pro302 primer

<400> SEQUENCE: 102
caggcgggtc tgggcccgta ttctatttct ggcctg 36

<210> SEQ ID NO 103
<211> LENGTH: 36
<212> TYPE: DNA
<213> ORGANISM: Artificial Sequence
<220> FEATURE:
<223> OTHER INFORMATION: Synthetic His302 primer

<400> SEQUENCE: 103
caggcgggtc tgggccatta ttctatttct ggcctg 36

<210> SEQ ID NO 104
<211> LENGTH: 36
<212> TYPE: DNA
<213> ORGANISM: Artificial Sequence
<220> FEATURE:
<223> OTHER INFORMATION: Synthetic Asp302 primer

<400> SEQUENCE: 104
caggcgggtc tgggcgatta ttctatttct ggcctg 36

<210> SEQ ID NO 105
<211> LENGTH: 36
<212> TYPE: DNA
<213> ORGANISM: Artificial Sequence
<220> FEATURE:
<223> OTHER INFORMATION: Synthetic Met302 primer

<400> SEQUENCE: 105
caggcgggtc tgggcatgta ttctatttct ggcctg 36

<210> SEQ ID NO 106
<211> LENGTH: 36
<212> TYPE: DNA
<213> ORGANISM: Artificial Sequence
<220> FEATURE:
<223> OTHER INFORMATION: Synthetic Thr302 primer

<400> SEQUENCE: 106
caggcgggtc tgggcaccta ttctatttct ggcctg 36

<210> SEQ ID NO 107
<211> LENGTH: 36
<212> TYPE: DNA
<213> ORGANISM: Artificial Sequence
<220> FEATURE:
<223> OTHER INFORMATION: Synthetic Gln302 primer

<400> SEQUENCE: 107
caggcgggtc tgggccagta ttctatttct ggcctg 36

<210> SEQ ID NO 108
<211> LENGTH: 36
<212> TYPE: DNA
<213> ORGANISM: Artificial Sequence
<220> FEATURE:
<223> OTHER INFORMATION: Synthetic Arg302 primer

<400> SEQUENCE: 108
caggcgggtc tgggccgtta ttctatttct ggcctg 36

<210> SEQ ID NO 109
<211> LENGTH: 36
<212> TYPE: DNA
<213> ORGANISM: Artificial Sequence
<220> FEATURE:
<223> OTHER INFORMATION: Synthetic Ser302 primer

<400> SEQUENCE: 109
caggcgggtc tgggcagcta ttctatttct ggcctg 36

<210> SEQ ID NO 110
<211> LENGTH: 456
<212> TYPE: PRT
<213> ORGANISM: Artificial Sequence
<220> FEATURE:
<223> OTHER INFORMATION: Synthetic cfrA-A184W-Y279K-E302Q-R305I

<400> SEQUENCE: 110

Met Asp Lys Glu Lys Ser Asn Asn Asp Lys Pro Ala Thr Lys Ile Asn
1 5 10 15

Arg Arg Gln Phe Leu Lys Phe Gly Ala Gly Ala Ser Ser Gly Ile Ala
20 25 30

-continued

```
Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Trp Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Lys His Ala Val Pro Ile Gly Ser Asp Ser
        275                 280                 285

Ala Leu Ala Ile Pro Ile Ala Ile Gln Ala Gly Leu Gly Gln Tyr Ser
    290                 295                 300

Ile Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
                325                 330                 335

Phe Gly Val Thr Glu Phe Cys Lys Thr Cys Lys Lys Cys Ala Glu Ala
            340                 345                 350

Cys Ala Pro Gln Ala Ile Ser Tyr Glu Asp Pro Thr Ile Asp Gly Pro
        355                 360                 365

Arg Gly Gln Met Gln Asn Ser Gly Ile Lys Arg Trp Tyr Val Asp Pro
    370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
            420                 425                 430

Met Lys Asp Met Asp Asp Ile Phe Gly Tyr Gly Lys Leu Asn Asp Glu
        435                 440                 445

Lys Ala Ile Ala Asp Trp Trp Lys
```

450 455

<210> SEQ ID NO 111
<211> LENGTH: 1371
<212> TYPE: DNA
<213> ORGANISM: Artificial Sequence
<220> FEATURE:
<223> OTHER INFORMATION: Synthetic cfrA-A184W-Y279K-E302Q-R305I

<400> SEQUENCE: 111
atggacaaag agaaatccaa caacgacaaa ccggcgacca agatcaaccg ccgccagttc 60
ctgaaattcg gcgcaggtgc atctagcggt atcgctatcg caactgcagc aactgcactg 120
ggtggcaaat ccctgatcga tcctaaacag gtgtacgcag gtactgtgaa agagctggac 180
gagctgccgt tcaacatccc tgcagactac aaaccgttca ctaaccagcg taacatctac 240
ggccaggcag tactgggtgt acctgagcct ctggcactgg tagaacgctt tgacgaagta 300
cgttggaacg gttggcaaac tgacggttct ccaggtctga ccgttctgga tggtgcagct 360
gcgcgtgcta gctttgctgt tgattattac ttcaacggcg agaactctgc ttgccgtgct 420
aacaagggtt tcttcgagtg gcacccgaaa gtggctgaac tgaacttcaa atggggcgac 480
ccagaacgta acatccacag cccaggtgtc aaatccgctg aagaaggtac catggctgtg 540
aagaagatct ggcgtttctt cggtgctgct aaagcgggta tcgctccatt cgacaaacgt 600
tgggtcttca ccgaaaccta cgccttcgtg aagaccccag aaggtgaatc tctgaaattc 660
atcccgccgg acttcggctt cgaaccgaaa cacgttatca gcatgatcat cccgcagagc 720
ccggaaggtg tcaaatgcga cccgagcttt ctgggttcta ccgaatacgg tctgtcttgt 780
gctcaaatcg gttacgccgc cttcggtctg tctatgttca tcaaagacct gggcaaacac 840
gccgttccga ttggttctga cagcgccctg gccattccga ttgcgattca ggcgggtctg 900
ggccagtatt ctatttctgg cctgatgatt actccggaat ttggcagcaa cgttcgtctg 960
tgtgaagtgt ttacggatat gccgctgaac catgacaaac cgatctcctt cggcgttacc 1020
gaattctgta agacgtgcaa gaaatgcgcg gaagcgtgtg cgccgcaggc gatttcctat 1080
gaagacccga ccattgatgg cccgcgtggc cagatgcaga actccggcat caaacgctgg 1140
tatgttgatc cggtaaaatg tctggaattc atgtcccgcg ataatgttgg caattgctgc 1200
ggcgcgtgca ttgcggcgtg cccgtttacc aaaccggaag cgtggcatca caccctgatt 1260
cgctccctgg ttggcgcgcc ggttattacg ccgtttatga aagatatgga tgatatcttt 1320
ggctatggca aactgaatga tgagaaagcc atcgccgatt ggtggaaata g 1371

<210> SEQ ID NO 112
<211> LENGTH: 1049
<212> TYPE: PRT
<213> ORGANISM: Artificial Sequence
<220> FEATURE:
<223> OTHER INFORMATION: Synthetic cytochrome P450 protein from B.
megaterium

<400> SEQUENCE: 112

Met Thr Ile Lys Glu Met Pro Gln Pro Lys Thr Phe Gly Glu Leu Lys
1 5 10 15

Asn Leu Pro Leu Leu Asn Thr Asp Lys Pro Val Gln Ala Leu Met Lys
20 25 30

Ile Ala Asp Glu Leu Gly Glu Ile Phe Lys Phe Glu Ala Pro Gly Arg
35 40 45

Val Thr Arg Tyr Leu Ser Ser Gln Arg Leu Ile Lys Glu Ala Cys Asp

-continued

```
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480
```

-continued

```
Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895
```

-continued

```
Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045
```

DEHALOGENASE VARIANT PROTEIN, POLYNUCLEOTIDE ENCODING DEHALOGENASE VARIANT PROTEIN, RECOMBINANT MICROORGANISM INCLUDING POLYNUCLEOTIDE, COMPOSITION INCLUDING RECOMBINANT MICROORGANISM, AND METHOD OF REDUCING CONCENTRATION OF FLUORINATED METHANE USING DEHALOGENASE

CROSS-REFERENCE TO RELATED APPLICATION

This application claims the benefit of Korean Patent Application No. 10-2016-0133076, filed on Oct. 13, 2016, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 98,345 Byte ASCII (Text) file named "728134_ST25.TXT," created on Oct. 12, 2017.

BACKGROUND

1. Field

The present disclosure relates to a dehalogenase variant, a polynucleotide encoding the dehalogenase variant, a recombinant microorganism including the polynucleotide, a composition including the recombinant microorganism, and a method of reducing a concentration of fluorinated methane using the dehalogenase variant.

2. Description of the Related Art

One of the most serious environmental problems is the emission of greenhouse gases which accelerate global warming. Among the greenhouse gases, fluorinated gases (F-gas) such as perfluorocarbons (PFCs), hydrofluorocarbons (HFCs), and sulfur hexafluoride ($SF_6$) show low absolute emission but have a long half-life and a very high global warming potential, resulting in significant adverse environmental impacts. The amount of F-gas emitted from semiconductor and electronics industries, which are major sources of F-gas emission, has exceeded the assigned limits of greenhouse gas emissions and continues to increase. Therefore, costs required for degradation of greenhouse gases and greenhouse gas emission allowances are increasing every year. A pyrolysis or catalytic thermal oxidation process has generally been used for the decomposition of F-gas. However, this process has disadvantages in terms of limited decomposition rate, emission of secondary pollutants, and high cost. To help solve this problem, biological decomposition of F-gas using a microbial biocatalyst has been adopted, as this approach is expected to overcome the limitations of the chemical decomposition process and allow F-gas to be treated in a more economical and environmentally friendly manner.

Accordingly, there is a need to identify new enzymes and microbial biocatalysts for the biological decomposition of F-gas. This invention provides such enzymes and microbial biocatalysts.

SUMMARY

Provided is a dehalogenase variant having dehalogenase activity and an amino acid alteration at one or more amino acid residues corresponding to positions A184, Y279, E302, and R305 of SEQ ID NO: 1.

Also provided is polynucleotide encoding the dehalogenase variant.

Further provided is a recombinant microorganism including a genetic modification that increases dehalogenase activity. In one aspect, the recombinant microorganism includes an exogenous polynucleotide encoding the dehalogenase variant.

Additionally, the disclosure provides a method of reducing $CH_nF_{4-n}$ concentration in a sample, wherein n is an integer from 0 to 3, the method including contacting the sample containing $CH_nF_{4-n}$ with the dehalogenase variant provided herein to reduce the $CH_nF_{4-n}$ concentration in the sample.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
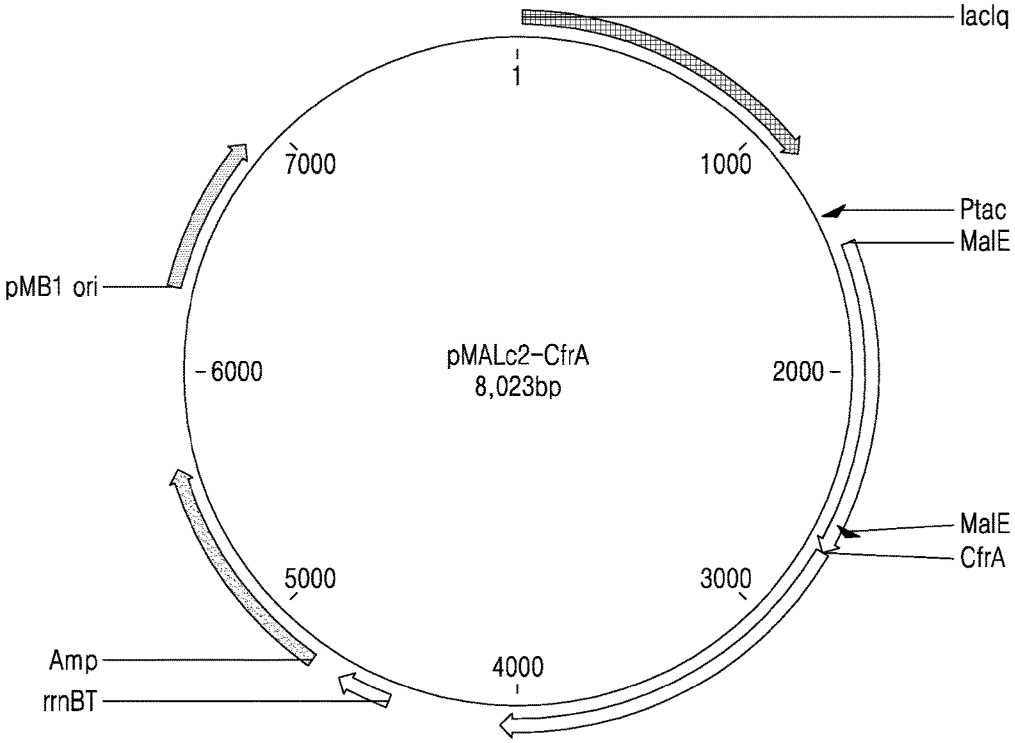
FIG. 1 shows a vector map of a pMAL-c2-CfrA vector.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items.

The term "increase in activity", or "increased activity", as used herein, may refer to a detectable increase in the activity of a cell, a polypeptide, a protein, or an enzyme. The term "increase in activity" or "increased activity" may also refer to an activity level of a modified (e.g., genetically engineered) cell, polypeptide, protein, or enzyme that is higher than that of a comparable cell, polypeptide, protein, or enzyme of the same type, such as a cell, polypeptide, protein, or enzyme that does not have a given genetic modification (e.g., the original or "wild-type" cell, polypeptide, protein, or enzyme). The term "activity of a cell" may refer to activity of a specific polypeptide, protein, or enzyme of the cell. For example, an activity level of the modified or engineered cell, polypeptide, protein, or enzyme may be increased by about 5% or greater, about 10% or greater, about 15% or greater, about 20% or greater, about 30% or greater, about 50% or greater, about 60% or greater, about 70% or greater, or about 100% or greater, as compared with that of an unmodified cell, polypeptide, protein, or enzyme of the same type, e.g., a wild-type cell, polypeptide, protein, or enzyme. An activity level of a specific polypeptide, protein, or enzyme of a cell may be increased by about 5% or greater, about 10% or greater, about 15% or greater, about 20% or greater, about 30% or greater, about 50% or greater, about 60% or greater, about 70% or greater, or about 100% or greater, as compared with that of the same polypeptide, protein, or enzyme of a parent cell, e.g., an unmodified cell. A cell having an increased activity of a polypeptide, protein, and enzyme may be identified by using a method known to those of ordinary skill in the art.

The term "parent cell" may refer to an original cell, e.g., a non-genetically engineered cell of the same type as the engineered microorganism. With regard to a specific genetic modification, the parent cell may be a cell not having the specific genetic modification. Thus, the parent cell may be a cell used as a starting material for producing a microorganism that is genetically engineered to have an increased activity of a given polypeptide or protein (e.g., a dehalogenase variant). The same comparison applies to different genetic modifications.

The term "gene" refers to a polynucleotide or a nucleic acid fragment expressing a specific protein, and may optionally include regulatory sequences such as a 5' non-coding sequence and/or a 3' non-coding sequence.

The term "polynucleotide" may comprehensively include DNA and RNA molecules, such as gDNA and cDNA. The term "nucleotide" refers to the basic structural unit of the polynucleotide, and may include any naturally occurring nucleotide and any analogue thereof having a modified sugar or base. The polynucleotide may be a separated polynucleotide.

The term "sequence identity" of a nucleic acid or polypeptide refers to a degree of identity between bases or amino acid residues of sequences obtained after the sequences are aligned so as to best match in specific comparable regions. The sequence identity is a value obtained by comparison of two sequences in specific comparable regions via optimal alignment of the two sequences, wherein portions of the sequences in the specific comparable regions may be added or deleted relative to reference sequences. A percentage of sequence identity may be calculated by, for example, comparing two optimally aligned sequences in the entire comparable regions, determining the number of locations in which the same amino acids or nucleotides appear to obtain the number of matching locations, dividing the number of matching locations by the total number of locations in the comparable regions (that is, the size of a range), and multiplying a result of the division by 100 to obtain the percentage of the sequence identity. The percentage of the sequence identity may be determined using a known sequence comparison program, for example, BLASTN (NCBI), BLASTP (NCBI), CLC Main Workbench (CLC bio), MegAlign™ (DNASTAR Inc), etc. Unless otherwise mentioned in the present disclosure, parameters used in the operation of the program are selected as follows: Ktuple=2, Gap Penalty=4, and Gap length penalty=12.

The term "genetic modification" refers to artificial alteration of the genetic material of a cell.

According to an aspect, a dehalogenase variant may have dehalogenase activity and include a variant of SEQ ID NO: 1, or homologs thereof. The dehalogenase variant (e.g., a dehalogenase comprising a variant of SEQ ID NO: 1) may have dehalogenase activity and include an amino acid alteration at one or more amino acid residues corresponding to positions A184, Y279, E302, and R305 of SEQ ID NO: 1.

A dehalogenase is an enzyme that catalyzes the removal of chlorine, bromine, or iodine atoms from a substrate. A chloroform reductive dehalogenase (CfrA) may be an enzyme classified as EC1.97.1.8. A dehalogenase enzyme may be derived from a microorganism of the genus *Dehalobacter*, such as *Dehalobacter* sp. CF, *Dehalobacter restrictus* PER K23, *Dehalobacter* sp. E1, *Dehalobacter* sp. TCA1, *Dehalobacter* sp. MS, or *Dehalobacter* sp. WL. In one embodiment the dehalogenase enzyme may be derived from *Dehalobacter* sp. In another embodiment the dehalogenase enzyme may be the chloroform reductive dehalogenase. In another embodiment the dehalogenase enzyme may be a polypeptide having the amino acid sequence of SEQ ID NO: 1.

Without wishing to be bound by any particular theory or mechanism of action, it is believed that the amino acid residues corresponding to positions A184, Y279, E302, and R305 of SEQ ID NO: 1 may be positioned more near to a substrate during catalysis as compared with amino acid residues at other positions of SEQ ID NO: 1. Thus, an amino acid alteration at one or more amino acid residues corresponding to position A184, Y279, E302, and R305 of SEQ ID NO: 1, is believed to reinforce binding to the substrate or shorten the distance from the substrate.

The amino acid alteration may be a substitution of one or more amino acid residues corresponding to positions A184, Y279, E302, and R305 of SEQ ID NO: 1 with a different amino acid, e.g., any of the 19 natural amino acids.

The amino acid alteration may be a substitution of the amino acid residue corresponding to position A184 of SEQ ID NO: 1 with W; a substitution of the amino acid residue corresponding to position Y279 of SEQ ID NO: 1 with K; a substitution of the amino acid residue corresponding to position E302 of SEQ ID NO: 1 with Q; or a substitution of the amino acid residue corresponding to position R305 of SEQ ID NO: 1 with I, Q, E, or S; or a combination thereof. The amino acid alteration may be substitution with at least one of A184W, Y279K, E302Q, R305I, R305Q, R305E, and R305S of the amino acid sequence of SEQ ID NO: 1.

The dehalogenase variant may have an amino acid alteration at an amino acid residue corresponding to position A184 of SEQ ID NO: 1, an A184W substitution, or an amino acid sequence of SEQ ID NO: 3.

The dehalogenase variant may have an amino acid alteration at an amino acid residue corresponding to position Y279 of SEQ ID NO: 1, an Y279K substitution, or an amino acid sequence of SEQ ID NO: 4.

The dehalogenase variant may have an amino acid alteration at an amino acid residue corresponding to position E302 of SEQ ID NO: 1, an E302Q substitution, or an amino acid sequence of SEQ ID NO: 5.

The dehalogenase variant may have an amino acid alteration at an amino acid residue corresponding to position R305 of SEQ ID NO: 1; an R305I, R305Q, R305E, or R305S substitution; or an amino acid sequence of SEQ ID NO: 6, 25, 26, or 27.

Each of the amino acid sequences of SEQ ID NOs: 3 to 6 and 25 to 27 are examples of a dehalogenase variant having an amino acid alteration at an amino acid residue corresponding to position A184, Y279, E302, or R305 of the amino acid sequence of SEQ ID NO: 1. In some embodiments, two, three, and four amino acid alterations may be selected from amino acid alterations at amino acid residues corresponding to positions A184, Y279, E302, and R305 of the amino acid sequence of SEQ ID NO: 1.

The dehalogenase variant may have increased dehalogenase activity as compared with that of a dehalogenase having the amino acid sequence of SEQ ID NO: 1 or a wild-type dehalogenase. The dehalogenase variant may have increased catalytic activity in relation to removal of fluorine atoms from a substrate. The dehalogenase variant may have increased activity for reducing a concentration of $CH_nF_{4-n}$ (n may be an integer from 0 to 3).

The amino acid sequence of the dehalogenase variant may have a sequence identity of 95% or greater, 96% or greater, 97% or greater, 98% or greater, or 99% or greater with the amino acid sequence of SEQ ID NO: 1 or SEQ ID NOs: 3 to 6 or 25 to 27, provided that one or more of A184, Y279, E302, and R305 are substituted as compared to SEQ ID NO: 1. In one embodiment, only one or more of one or more of A184, Y279, E302, and R305 are substituted as compared to SEQ ID NO: 1.

According to another aspect, a polynucleotide is provided that encodes the dehalogenase variant. The polynucleotide may encode a dehalogenase variant having dehalogenase activity and an amino acid alteration at one or more amino acid residues corresponding to positions A184, Y279, E302, and R305 of SEQ ID NO: 1.

The polynucleotide encoding a dehalogenase variant may be derived from a microorganism of the genus *Dehalobacter*, such as *Dehalobacter* sp. CF, *Dehalobacter restrictus* PER K23, *Dehalobacter* sp. E1, *Dehalobacter* sp. TCA1, *Dehalobacter* sp. MS, or *Dehalobacter* sp. WL.

The polynucleotide may be codon-optimized with respect to the recombinant microorganism acting as a host cell. Codon optimization refers to production of a gene in which one or more endogenous codons are replaced with codons for the same amino acid but of preference in the corresponding host.

The polynucleotide encoding the dehalogenase variant may be a gene encoding a variant having an A184W substitution in the amino acid sequence of SEQ ID NO: 1 or the amino acid sequence of SEQ ID NO: 3. This gene may have a nucleotide sequence of SEQ ID NO: 7.

The polynucleotide encoding the dehalogenase variant may be a gene encoding a variant having a Y279K substitution in the amino acid sequence of SEQ ID NO: 1 or the amino acid sequence of SEQ ID NO: 4. This gene may have a nucleotide sequence of SEQ ID NO: 8 or 9.

The polynucleotide encoding the dehalogenase variant may be a gene encoding a variant having an E302Q substitution in the amino acid sequence of SEQ ID NO: 1 or the amino acid sequence of SEQ ID NO: 5. This gene may have a nucleotide sequence of SEQ ID NO: 10 or 11.

The polynucleotide encoding the dehalogenase variant may be a gene encoding a variant having an R305I, R305Q, R305E, or R305Substitution in the amino acid sequence of SEQ ID NO: 1 or the amino acid sequence of SEQ ID NO: 6, 25, 26, or 27. This gene may have a nucleotide sequence of SEQ ID NO: 12, 13, or 14, a nucleotide sequence of SEQ ID NO: 15 or 16, a nucleotide sequence of SEQ ID NO: 17 or 18, or a nucleotide sequence of SEQ ID NO: 19, 20, 21, 22, 23, or 24.

The polynucleotide may be a nucleotide sequence of SEQ ID NO: 2 in which GCG is substituted with TGG at $550^{th}$ to $552^{nd}$ nucleotides thereof; TAC is substituted with AAA or AAG at $835^{th}$ to $837^{th}$ nucleotides thereof; GAA is substituted with CAA or CAG at $904^{th}$ to $906^{th}$ nucleotides thereof; CGT is substituted with ATT, ATC, or ATA at $913^{th}$ to $915^{th}$ nucleotides thereof; CGT is substituted with CAA or CAG at $913^{th}$ to $915^{th}$ nucleotides thereof; CGT is substituted with GAA or GAG at $913^{th}$ to $915^{th}$ nucleotides thereof; CGT is substituted with AGT, AGC, TCT, TCC, TCA, or TCG at $913^{th}$ to $915^{th}$ nucleotides thereof; or a combination thereof.

The term "corresponding" as used herein refers to an amino acid position of a protein of interest that aligns with the mentioned position (e.g., position A184, Y279, E302, or R305 of an amino acid sequence of SEQ ID NO: 1) of a reference protein when amino acid sequences (e.g., SEQ ID NO: 1) of the protein of interest and the reference protein are aligned using a protein alignment program acceptable in the art, such as the NCBI BLAST pairwise alignment or the well-known Lipman-Pearson Protein Alignment program, with the following alignment parameters. A database (DB) storing the reference sequence may be RefSeq non-redundant proteins of NCBI. Parameters used in the sequence alignment may be as follows: Ktuple=2, Gap Penalty=4, and Gap length penalty=12. In this regard, a range included in a "corresponding" sequence may be a range of E-value 0.00001 and H-value 0.001.

Examples of proteins (hereinafter, referred as "homologs of cfrA A184") having an alanine at the position corresponding to position A184 of SEQ ID NO: 1, obtained according to the above alignment conditions, are listed in Table 1.

TABLE 1

| No. | | NCBI ID |
|---|---|---|
| 1 | putative PceA [*Dehalobacter* sp. UNSWDHB] | EQB22800.1 |
| 2 | 1,1-dichloroethane reductive dehalogenase | WP_015043247.1 |

Examples of proteins (hereinafter, referred as "homologs of cfrA Y279") having a tyrosine at the position corresponding to position Y279 of SEQ ID NO: 1, obtained according to the above alignment conditions, are listed in Table 2.

TABLE 2

| No. | | NCBI ID |
|---|---|---|
| 1 | 1,1-dichloroethane dehalogenase | WP_034377773.1 |
| 2 | chloroform and 1,1,1-trichloroethane reductive dehalogenase | AGO27983.1 |

Examples of proteins (hereinafter, referred as "homologs of cfrA E302") having a glutamic acid at the position corresponding to position E302 of SEQ ID NO: 1, obtained according to the above alignment conditions, are listed in Table 3.

TABLE 3

| No. | | NCBI ID |
|---|---|---|
| 1 | 1,1-dichloroethane dehalogenase [*Dehalobacter restrictus*] | WP_025205280.1 |
| 2 | reductive dehalogenase [*Desulfosporosinus orientis* DSM 765] | AET69295.1 |

Examples of proteins (hereinafter, referred as "homologs of cfrA R305") having an arginine at the position corresponding to position R305 of SEQ ID NO: 1, obtained according to the above alignment conditions, are listed in Table 4.

TABLE 4

| No. | | NCBI ID |
|---|---|---|
| 1 | dehalogenase [*Gracilibacter* sp. BRH_c7a] | KUO60930.1 |
| 2 | reductive dehalogenase [*Dehalobacter*] | WP_015044413.1 |

According to still another aspect, a vector including a polynucleotide encoding the dehalogenase variant is provided. The polynucleotide may be operably linked to a regulatory sequence. The regulatory sequence may include a promoter, a terminator, an enhancer, or a combination thereof. The term "operably linked" refers to a gene that needs to be expressed being functionally bound to a regulatory sequence thereof so that the gene may be expressed. The vector may further include a replication origin, a transcriptional regulatory region, a multiple cloning site, a selectable marker, or a combination thereof.

According to still another aspect, a recombinant microorganism may include a genetic modification for increasing dehalogenase activity. The genetic modification may include a gene encoding the dehalogenase variant. The genetic modification may include a gene encoding a dehalogenase variant having dehalogenase activity and an amino acid alteration at one or more amino acid residues corresponding to positions A184, Y279, E302, and R305 of SEQ ID NO: 1. The recombinant microorganism may include at least one exogenous gene encoding a dehalogenase variant having dehalogenase activity and at least one an amino acid alteration in at least one amino acid residue corresponding to positions A184, Y279, E302, and R305 of SEQ ID NO: 1. The amino acid alteration may be substitution with A184W, Y279K, E302Q, R305I, R305Q, R305E, or R305S of SEQ ID NO: 1, or a combination thereof.

The gene may be a polynucleotide selected from a nucleotide sequence of SEQ ID NO: 2 in which GCG is substituted with TGG at $550^{th}$ to $552^{nd}$ nucleotides thereof; TAC is substituted with AAA or AAG at $835^{th}$ to $837^{th}$ nucleotides thereof; GAA is substituted with CAA or CAG at $904^{th}$ to $906^{th}$ nucleotides thereof; CGT is substituted with ATT, ATC, or ATA at $913^{th}$ to $915^{th}$ nucleotides thereof; CGT is substituted with CAA or CAG at $913^{th}$ to $915^{th}$ nucleotides thereof; CGT is substituted with GAA or GAG at $913^{th}$ to $915^{th}$ nucleotides thereof; CGT is substituted with AGT, AGC, TCT, TCC, TCA, or TCG at $913^{th}$ to $915^{th}$ nucleotides thereof; and a combination thereof.

The term "exogenous gene" refers to a gene that is externally introduced into a cell, and may be, for example, homologous or heterologous with respect to a host cell into which the gene is introduced. The term "heterologous" as used herein refers to "foreign" or "not native".

The recombinant microorganism may include one or more, for example, 2 or more, 3 or more, 4 or more, 5 or more, 10 or more, or 50 or more exogenous genes encoding the dehalogenase variant. When a plurality of genes are included in the recombinant microorganism, the plurality of genes may be different from each other. The gene may be integrated into the genome of the recombinant microorganism, or may be independent of the genome.

The recombinant microorganism may include a prokaryotic cell, a eukaryotic cell, or an organism of a microscopic size. The recombinant microorganism may include a eukaryotic microorganism such as that of Archaea, eubacteria, or yeast and fungi. The recombinant microorganism may be cultured under anaerobic conditions.

The recombinant microorganism may be bacteria or fungi. The bacteria may be gram-positive or gram-negative bacteria. The bacteria may belong to the family Enterobacteriaceae. The bacteria may belong to the genus *Escherichia*, the genus *Salmonella*, the genus *Xanthomonas*, or the genus *Pseudomonas*. The bacteria may belong to the genus *Bacillus*, the genus *Xanthobacter*, the genus *Azotobacter*, or the genus *Agrobacterium*. The recombinant microorganism may be *Escherichia coli* or *Xanthobacter autotrophicus*.

The recombinant microorganism, into which a gene encoding a dehalogenase variant is introduced, may have increased dehalogenase activity as compared with a parent strain (e.g., a microorganism including a gene encoding a dehalogenase having an amino acid sequence of SEQ ID NO: 1). The recombinant microorganism, into which a gene encoding a dehalogenase variant is introduced, may have increased catalytic activity for removal of fluorine atoms from a substrate, as compared with a parent strain. The recombinant microorganism, into which a gene encoding a dehalogenase variant is introduced, may greatly reduce a concentration of $CH_nF_{4-n}$ (n may be an integer from 0 to 3), as compared with a parent strain.

The recombinant microorganism may further include at least one exogenous gene that encodes bacterial cytochrome P450, a tetrachloroethene reductive dehalogenase, a dichloromethane dehalogenase, a haloalkane dehalogenase, an alkyl halidase, a haloacid dehalogenase, a haloacetate dehalogenase, or a combination thereof. The cytochrome P450 protein may belong to EC 1.14.15.1 or EC 1.14.14.1. Bacterial cytochromes P450 may be Cytochrome P450 BM3 (CYP102) derived from *B. megaterium*. The cytochrome P450 protein may have an amino acid sequence of SEQ ID NO:112.

With regard to the recombinant microorganism, the gene may be introduced into the microorganism by a general method known in the art, for example, transformation or electroporation.

According to still another aspect, a composition may include the dehalogenase variant for reducing a concentration of $CH_nF_{4-n}$ (n may be an integer from 0 to 3) in a sample. The composition may include a dehalogenase variant for reducing a concentration of $CH_nF_{4-n}$ (n may be an integer from 0 to 3) in a sample, wherein the dehalogenase variant may have dehalogenase activity and an amino acid alteration at one or more amino acid residues corresponding to positions A184, Y279, E302, and R305 of SEQ ID NO: 1.

The amino acid alteration may be a substitution of the amino acid residue corresponding to position A184 with W; a substitution of the amino acid residue corresponding to position Y279 with K; a substitution of the amino acid residue corresponding to position E302 with Q; a substitution of the amino acid residue corresponding to position R305 with I, Q, E, or S; or a combination thereof. The amino acid alteration may be substitution with A184W, Y279K, E302Q, R305I, R305Q, R305E, or R305S of SEQ ID NO: 1, or a combination thereof.

The dehalogenase variant may be in a recombinant microorganism including a dehalogenase variant expressed from an exogenous gene. The dehalogenase variant may be in a recombinant microorganism including an exogenous polynucleotide encoding the dehalogenase variant. The dehalogenase variant may be in a recombinant microorganism expressing the dehalogenase variant, a lysate thereof, a water-soluble material fraction of the lysate, the recombinant dehalogenase variant alone, or combination thereof. The dehalogenase variant may be expressed from an exogenous gene. The composition may further include a material increasing solubility of fluorinated methane represented by $CH_nF_{4-n}$ (n may be an integer from 0 to 3) in a medium or culture medium.

The term "reducing" refers to a decrease of a concentration of fluorinated methane in a sample, and includes partial removal or full removal. The composition may reduce a concentration of fluorinated methane represented by $CH_nF_{4-n}$ (n may be an integer from 0 to 3) in a sample. The reducing of a concentration of fluorinated methane may include cleaving C—F bonds of fluorinated methane, converting fluorinated methane into other materials, or reducing the concentration of fluorinated methane in the sample by intracellular accumulation. The converting may be introducing a hydrophilic group such as a hydroxyl group into fluorinated methane, or introducing a carbon-carbon double bond or a carbon-carbon triple bond thereto.

The sample may be in a liquid or gas state. The sample may be industrial waste water or waste gas. The sample may be any material that includes the fluorinated methane. The fluorinated methane may be $CF_4$, $CHF_3$, $CH_2F_2$, $CH_3F$, or a mixture thereof.

According to an aspect, a method of reducing $CH_nF_{4-n}$ concentration in a sample, wherein n may be an integer from 0 to 3, may include contacting a sample containing $CH_nF_{4-n}$ with the dehalogenase variant. A method of reducing $CH_nF_{4-n}$ concentration (n may be an integer from 0 to 3) in the sample may include contacting the sample containing $CH_nF_{4-n}$ with the dehalogenase variant to reduce $CH_nF_{4-n}$ concentration in the sample, wherein the dehalogenase variant may have dehalogenase activity and an amino acid alteration at one or more amino acid residues corresponding to positions A184, Y279, E302, and R305 of SEQ ID NO: 1.

The dehalogenase variant may be in a recombinant microorganism including a dehalogenase variant expressed from an exogenous gene. The dehalogenase variant may be in a recombinant microorganism including an exogenous polynucleotide encoding the dehalogenase variant. The dehalogenase variant may be in a recombinant microorganism expressing the dehalogenase variant, a lysate thereof, a water-soluble material fraction of the lysate, the recombinant dehalogenase variant alone, or combination thereof. The lysate refers to a state in which the microorganism is broken up so that contents thereof are exposed to the outside of a cell. The lysate may be obtained by breaking up a cell by using an enzyme, heat, or pressure. The lysate may include the recombinant microorganism extract, recombinant protein extract, or crude extracts thereof. A gene may be introduced into the recombinant microorganism, the gene encoding a dehalogenase variant having dehalogenase activity and an amino acid alteration at one or more amino acid residues corresponding to positions A184, Y279, E302, and R305 of SEQ ID NO: 1.

The contacting the sample with the dehalogenase variant may include culturing or incubating the recombinant microorganism, a lysate thereof, or a fraction of the lysate thereof with the sample containing $CH_nF_{4-n}$ (n may be an integer from 0 to 3), wherein the recombinant microorganism may include a dehalogenase variant expressed from an exogenous gene.

The contacting the sample with the dehalogenase variant may be performed in a sealed container. The contacting the sample with the dehalogenase variant may include culturing a recombinant microorganism, a lysate thereof, or a fraction of the lysate thereof with the sample in a sealed container (e.g., air-sealed, liquid-sealed, or both depending on the nature of the sample). The term "sealed" as used herein refers to state substantially or completely fastened or closed securely. The contacting the sample with the dehalogenase variant may include culturing a recombinant microorganism with the sample in a sealed container under conditions in which the recombinant microorganism may be allowed to proliferate, wherein the recombinant microorganism may include a dehalogenase variant expressed from an exogenous gene. The contacting may be gas-liquid contact in which a gas sample is contacted with a liquid containing a dehalogenase variant. The contacting may also be liquid-liquid contact in which a liquid sample is contacted with a liquid containing a dehalogenase variant. The contacting may be performed, for example, by contacting a culture medium in which the recombinant microorganism is being cultured with the sample. The liquid-liquid contact may include mixing.

The contacting may be performed under aerobic or anaerobic conditions. The contacting may be performed in a sealed container under conditions in which the recombinant microorganism may survive or be viable. The conditions in which the recombinant microorganism may survive or be viable may be conditions in which the recombinant microorganism may be allowed to proliferate or remain in a resting state. For example, the contacting may be culturing of the recombinant microorganism in the presence of fluorinated methane. The contacting may be performed during an exponential phase or a stationary phase of a growth stage of the recombinant microorganism.

The contacting may be performed in a batch or continuous manner. The contacting may include, for example, contacting a fresh recombinant microorganism with fluorinated methane in the sample. The contacting with the fresh recombinant microorganism may be performed twice or more, for example, twice, three times, five times, or ten times or more. The contacting may be continued or repeated until a concentration of fluorinated methane represented by $CH_nF_{4-n}$ (where n may be an integer from 0 to 3) in the sample reaches a desired reduced concentration.

Hereinafter, the inventive concept of the present disclosure will be described in greater detail with reference to Examples. However, these Examples are provided for illustrative purposes only, and the scope of the present disclosure is not intended to be limited by these Examples.

EXAMPLE

*Escherichia coli* Expressing Dehalogenase Variant and Decomposition of Fluorinated Carbon in Sample using the Same 1: Alteration of Nucleotide Sequence in Dehalogenase A dehalogenase gene was prepared by synthesizing DNA codon-optimized for *Escherichia coli* based on a chloroform reductive dehalogenase (CfrA) gene of a genus *Dehalobacter* strain (available from Cosmogenetech, Seoul, Korea).

The CfrA gene has a nucleotide sequence of SEQ ID NO: 2, and the CfrA gene encodes the amino acid sequence of SEQ ID NO: 1. In order to improve dehalogenase activity, screening was performed on the amino acid sequence of SEQ ID NO: 1 to find amino acid positions which are situated at a short distance from a substrate, as a result of the screening, four amino acid positions were selected.

In order to substitute an amino acid corresponding to a position n in the amino acid sequence of SEQ ID NO: 1 with a different amino acid, nucleotides encoding the position n amino acid of the nucleotide sequence of SEQ ID NO: 2 were substituted with nucleotides encoding one of 19 different natural amino acids. Some nucleotides directly adjacent to the altered nucleotide sequence were amplified multiple times. Amplification of nucleotides was performed from the first nucleotide to the nucleotide encoding the n-$1^{th}$ amino acid of the nucleotide sequence of SEQ ID NO: 2. In addition, amplification of nucleotides was performed from an arbitrary nucleotide positioned before the 5'-end of the substituted nucleotide to the nucleotides encoding the stop codon.

1-1: Alteration of Nucleotides for Amino Acid Alteration of R305 in SEQ ID NO: 1

The following is the detailed process thereof. In order to change an amino acid corresponding to position R305 in the amino acid sequence of SEQ ID NO: 1 to a different amino acid, CGT at the $913^{th}$ to $915^{th}$ nucleotides of the nucleotide sequence of SEQ ID NO: 2 were substituted with nucleotides encoding one of 19 different natural amino acids.

Some nucleotides directly adjacent to the substituted $913^{th}$ to $915^{th}$ nucleotides were amplified multiple times. The $1^{st}$ to $912^{th}$ nucleotides of the nucleotide sequence of SEQ ID NO: 2 were amplified using a DNA polymerase (primestar MAX, available from Takara Korea Biomedical Inc.) and primers having SEQ ID NOs: 28 and 30. In addition, the $898^{th}$ nucleotide to the nucleotides encoding the stop codon, including the substituted $913^{th}$ to $915^{th}$ nucleotides, were amplified using a DNA polymerase (primestar MAX, available from Takara Korea Biomedical Inc.) and primers having any one of SEQ ID NOs: 31 to 49 and SEQ ID NO: 29.

TABLE 5

| Primer | SEQ ID NO. | Primer sequence 5'- |
|---|---|---|
| CfrA-F | SEQ ID NO: 28 | atcgagggaaggatttcagaattcATGGACAAAGAGAAATCCAA |
| CfrA-R | SEQ ID NO: 29 | gtcgactctagaggatccgaattcTTACTATTTCCACCAATCGG |
| 305 PMR | SEQ ID NO: 30 | AGAATATTCGCCCAGACC |
| Phe305 | SEQ ID NO: 31 | CTGGGCGAATATTCTtttTCTGGCCTGATGATTACTC |
| Val305 | SEQ ID NO: 32 | CTGGGCGAATATTCTgtgTCTGGCCTGATGATTACTC |
| Ala305 | SEQ ID NO: 33 | CTGGGCGAATATTCTgcgTCTGGCCTGATGATTACTC |
| Asn305 | SEQ ID NO: 34 | CTGGGCGAATATTCTaacTCTGGCCTGATGATTACTC |
| Cys305 | SEQ ID NO: 35 | CTGGGCGAATATTCTtgcTCTGGCCTGATGATTACTC |
| Leu305 | SEQ ID NO: 36 | CTGGGCGAATATTCTcugTCTGGCCTGATGATTACTC |
| Gly305 | SEQ ID NO: 37 | CTGGGCGAATATTCTggcTCTGGCCTGATGATTACTC |
| Tyr305 | SEQ ID NO: 38 | CTGGGCGAATATTCTtatTCTGGCCTGATGATTACTC |
| Lys305 | SEQ ID NO: 39 | CTGGGCGAATATTCTaaaTCTGGCCTGATGATTACTC |
| Trp305 | SEQ ID NO: 40 | CTGGGCGAATATTCTtggTCTGGCCTGATGATTACTC |
| Ile305 | SEQ ID NO: 41 | CTGGGCGAATATTCTattTCTGGCCTGATGATTACTC |
| Pro305 | SEQ ID NO: 42 | CTGGGCGAATATTCTccgTCTGGCCTGATGATTACTC |
| His305 | SEQ ID NO: 43 | CTGGGCGAATATTCTcatTCTGGCCTGATGATTACTC |
| Asp305 | SEQ ID NO: 44 | CTGGGCGAATATTCTgatTCTGGCCTGATGATTACTC |
| Met305 | SEQ ID NO: 45 | CTGGGCGAATATTCTatgTCTGGCCTGATGATTACTC |
| Thr305 | SEQ ID NO: 46 | CTGGGCGAATATTCTaccTCTGGCCTGATGATTACTC |
| Gln305 | SEQ ID NO: 47 | CTGGGCGAATATTCTcagTCTGGCCTGATGATTACTC |
| Glu305 | SEQ ID NO: 48 | CTGGGCGAATATTCTgaaTCTGGCCTGATGATTACTC |
| Ser305 | SEQ ID NO: 49 | CTGGGCGAATATTCTagcTCTGGCCTGATGATTACTC |

Nucleotides of the nucleotide sequence of SEQ ID NO: 2 encoding amino acids corresponding to positions A184, Y279, and E302 of SEQ ID NO: 1 were respectively substituted with nucleotides encoding one of 19 different natural amino acids, in substantially the same manner as described above.

1-2: Alteration of Nucleotides for Amino Acid Alteration of A184 in SEQ ID NO: 1

In order to change an amino acid corresponding to position A184 in the amino acid sequence of SEQ ID NO: 1 to a different amino acid, GCG at the $550^{th}$ to $552^{nd}$ nucleotides of the nucleotide sequence of SEQ ID NO: 2 were substituted with nucleotides encoding one of 19 different natural amino acids.

Some nucleotides directly adjacent to the substituted $550^{th}$ to $552^{nd}$ nucleotides were amplified multiple times.

The $1^{st}$ to $549^{th}$ nucleotides of the nucleotide sequence of SEQ ID NO: 2 were amplified using a DNA polymerase (primestar MAX, available from Takara Korea Biomedical Inc.) and primers having SEQ ID NOs: 28 and 50. In addition, the $532^{th}$ nucleotide to the nucleotides encoding the stop codon, including the substituted $550^{th}$ to $552^{nd}$ nucleotides, were amplified using a DNA polymerase (primestar MAX, available from Takara Korea Biomedical Inc.) and primers having any one of SEQ ID NOs: 51 to 69 and SEQ ID NO: 29.

TABLE 6

| Primer | SEQ ID NO. | Primer sequence |
|---|---|---|
| CfrA-F | SEQ ID NO: 28 | atcgagggaaggatttcagaattcATGGACAAAGAGAAATCCAA |
| CfrA-R | SEQ ID NO: 29 | gtcgactctagaggatccgaattcTTACTATTTCCACCAATCGG |
| 184 PMR | SEQ ID NO: 50 | GATCTTCTTCACAGCCAT |
| Phe184 | SEQ ID NO: 51 | ATGGCTGTGAAGAAGATCtttCGTTTCTTCGGTGCTG |
| Val184 | SEQ ID NO: 52 | ATGGCTGTGAAGAAGATCgtgCGTTTCTTCGGTGCTG |
| Glu184 | SEQ ID NO: 53 | ATGGCTGTGAAGAAGATCgaaCGTTTCTTCGGTGCTG |
| Asn184 | SEQ ID NO: 54 | ATGGCTGTGAAGAAGATCaacCGTTTCTTCGGTGCTG |
| Cys184 | SEQ ID NO: 55 | ATGGCTGTGAAGAAGATCtgcCGTTTCTTCGGTGCTG |
| Leu184 | SEQ ID NO: 56 | ATGGCTGTGAAGAAGATCctgCGTTTCTTCGGTGCTG |
| Gly184 | SEQ ID NO: 57 | ATGGCTGTGAAGAAGATCggcCGTTTCTTCGGTGCTG |
| Tyr184 | SEQ ID NO: 58 | ATGGCTGTGAAGAAGATCtatCGTTTCTTCGGTGCTG |
| Lys184 | SEQ ID NO: 59 | ATGGCTGTGAAGAAGATCaaaCGTTTCTTCGGTGCTG |
| Trp184 | SEQ ID NO: 60 | ATGGCTGTGAAGAAGATCtggCGTTTCTTCGGTGCTG |
| Ile184 | SEQ ID NO: 61 | ATGGCTGTGAAGAAGATCattCGTTTCTTCGGTGCTG |
| Pro184 | SEQ ID NO: 62 | ATGGCTGTGAAGAAGATCccgCGTTTCTTCGGTGCTG |
| His184 | SEQ ID NO: 63 | ATGGCTGTGAAGAAGATCcatCGTTTCTTCGGTGCTG |
| Asp184 | SEQ ID NO: 64 | ATGGCTGTGAAGAAGATCgatCGTTTCTTCGGTGCTG |
| Met184 | SEQ ID NO: 65 | ATGGCTGTGAAGAAGATCatgCGTTTCTTCGGTGCTG |
| Thr184 | SEQ ID NO: 66 | ATGGCTGTGAAGAAGATCaccCGTTTCTTCGGTGCTG |
| Gln184 | SEQ ID NO: 67 | ATGGCTGTGAAGAAGATCcagCGTTTCTTCGGTGCTG |
| Arg184 | SEQ ID NO: 68 | ATGGCTGTGAAGAAGATCcgtCGTTTCTTCGGTGCTG |
| Ser184 | SEQ ID NO: 69 | ATGGCTGTGAAGAAGATCagcCGTTTCTTCGGTGCTG |

1-3: Alteration of Nucleotides for Amino Acid Alteration of Y279 in SEQ ID NO: 1

In order to change an amino acid corresponding to position Y279 in the amino acid sequence of SEQ ID NO: 1 to a different amino acid, TAC at the $835^{th}$ to $837^{th}$ nucleotides of the nucleotide sequence of SEQ ID NO: 2 were substituted with nucleotides encoding one of 19 different natural amino acids.

Some nucleotides directly adjacent to the substituted $835^{th}$ to $837^{th}$ nucleotides were amplified multiple times. The $1^{st}$ to $834^{th}$ nucleotides of the nucleotide sequence of SEQ ID NO: 2 were amplified using a DNA polymerase (primestar MAX, available from Takara Korea Biomedical Inc.) and primers having SEQ ID NOs: 28 and 70. In addition, the $819^{th}$ nucleotide to the nucleotides encoding the stop codon, including the substituted $835^{th}$ to $837^{th}$ nucleotides, were amplified using a DNA polymerase (primestar MAX, available from Takara Korea Biomedical Inc.) and primers having any one of SEQ ID NOs: 71 to 89 and SEQ ID NO: 29.

TABLE 7

| Primer | SEQ ID NO. | Primer sequence |
|---|---|---|
| CfrA-F | SEQ ID NO: 28 | atcgagggaaggatttcagaattcATGGACAAAGAGAAATCCAA |
| CfrA-R | SEQ ID NO: 29 | gtcgactctagaggatccgaattcTTACTATTTCCACCAATCGG |
| 279 PMR | SEQ ID NO: 70 | GCCCAGGTCTTTGATG |
| Phe279 | SEQ ID NO: 71 | CATCAAAGACCTGGGCtttCACGCCGTTCCGATT |

TABLE 7-continued

| Primer | SEQ ID NO. | Primer sequence |
|---|---|---|
| Val279 | SEQ ID NO: 72 | CATCAAAGACCTGGGCgtgCACGCCGTTCCGATT |
| Ala279 | SEQ ID NO: 73 | CATCAAAGACCTGGGCgcgCACGCCGTTCCGATT |
| Asn279 | SEQ ID NO: 74 | CATCAAAGACCTGGGCaacCACGCCGTTCCGATT |
| Cys279 | SEQ ID NO: 75 | CATCAAAGACCTGGGCtgcCACGCCGTTCCGATT |
| Leu279 | SEQ ID NO: 76 | CATCAAAGACCTGGGCctgCACGCCGTTCCGATT |
| Gly279 | SEQ ID NO: 77 | CATCAAAGACCTGGGCggcCACGCCGTTCCGATT |
| Tyr279 | SEQ ID NO: 78 | CATCAAAGACCTGGGCtatCACGCCGTTCCGATT |
| Lys279 | SEQ ID NO: 79 | CATCAAAGACCTGGGCaaaCACGCCGTTCCGATT |
| Trp279 | SEQ ID NO: 80 | CATCAAAGACCTGGGCtggCACGCCGTTCCGATT |
| Ile279 | SEQ ID NO: 81 | CATCAAAGACCTGGGCattCACGCCGTTCCGATT |
| Pro279 | SEQ ID NO: 82 | CATCAAAGACCTGGGCccgCACGCCGTTCCGATT |
| His279 | SEQ ID NO: 83 | CATCAAAGACCTGGGCcatCACGCCGTTCCGATT |
| Asp279 | SEQ ID NO: 84 | CATCAAAGACCTGGGCgatCACGCCGTTCCGATT |
| Met279 | SEQ ID NO: 85 | CATCAAAGACCTGGGCatgCACGCCGTTCCGATT |
| Thr279 | SEQ ID NO: 86 | CATCAAAGACCTGGGCaccCACGCCGTTCCGATT |
| Gln279 | SEQ ID NO: 87 | CATCAAAGACCTGGGCcagCACGCCGTTCCGATT |
| Glu279 | SEQ ID NO: 88 | CATCAAAGACCTGGGCgaaCACGCCGTTCCGATT |
| Ser279 | SEQ ID NO: 89 | CATCAAAGACCTGGGCagcCACGCCGTTCCGATT |

1-4: Alteration of Nucleotides for Amino Acid Alteration of E302 in SEQ ID NO: 1

In order to change an amino acid corresponding to position E302 in the amino acid sequence of SEQ ID NO: 1 to a different amino acid, GAA at the $904^{th}$ to $906^{th}$ nucleotides of the nucleotide sequence of SEQ ID NO: 2 were substituted with nucleotides encoding one of 19 different natural amino acids.

Some nucleotides directly adjacent to the substituted $904^{th}$ to $906^{th}$ nucleotides were amplified multiple times. The $1^{st}$ to $903^{th}$ nucleotides of the nucleotide sequence of SEQ ID NO: 2 were amplified using a DNA polymerase (primestar MAX, available from Takara Korea Biomedical Inc.) and primers having SEQ ID NOs: 28 and 90. In addition, the $889^{th}$ nucleotide to the nucleotides encoding the stop codon, including the substituted $904^{th}$ to $906^{th}$ nucleotides, were amplified using a DNA polymerase (primestar MAX, available from Takara Korea Biomedical Inc.) and primers having any one of SEQ ID NOs: 91 to 109 and SEQ ID NO: 29.

TABLE 8

| Primer | SEQ ID NO. | Primer sequence |
|---|---|---|
| CfrA-F | SEQ ID NO: 28 | atcgagggaaggatttcagaattcATGGACAAAGAGAAATCCAA |
| CfrA-R | SEQ ID NO: 29 | gtcgactctagaggatccgaattcTTACTATTTCCACCAATCGG |
| 302 PMR | SEQ ID NO: 90 | GCCCAGACCCGCCTG |
| Phe302 | SEQ ID NO: 91 | CAGGCGGGTCTGGGCtttTATTCTatTTCTGGCCTG |
| Val302 | SEQ ID NO: 92 | CAGGCGGGTCTGGGCgtgTATTCTatTTCTGGCCTG |
| Ala302 | SEQ ID NO: 93 | CAGGCGGGTCTGGGCgcgTATTCTatTTCTGGCCTG |
| Asn302 | SEQ ID NO: 94 | CAGGCGGGTCTGGGCaacTATTCTatTTCTGGCCTG |
| Cys302 | SEQ ID NO: 95 | CAGGCGGGTCTGGGCtgcTATTCTatTTCTGGCCTG |
| Leu302 | SEQ ID NO: 96 | CAGGCGGGTCTGGGCctgTATTCTatTTCTGGCCTG |
| Gly302 | SEQ ID NO: 97 | CAGGCGGGTCTGGGCggcTATTCTatTTCTGGCCTG |

TABLE 8-continued

| Primer | SEQ ID NO. | Primer sequence |
|---|---|---|
| Tyr302 | SEQ ID NO: 98 | CAGGCGGGTCTGGGCtatTATTCTatTTCTGGCCTG |
| Lys302 | SEQ ID NO: 99 | CAGGCGGGTCTGGGCaaaTATTCTatTTCTGGCCTG |
| Trp302 | SEQ ID NO: 100 | CAGGCGGGTCTGGGCtggTATTCTatTTCTGGCCTG |
| Ile302 | SEQ ID NO: 101 | CAGGCGGGTCTGGGCattTATTCTatTTCTGGCCTG |
| Pro302 | SEQ ID NO: 102 | CAGGCGGGTCTGGGCccgTATTCTatTTCTGGCCTG |
| His302 | SEQ ID NO: 103 | CAGGCGGGTCTGGGCcatTATTCTatTTCTGGCCTG |
| Asp302 | SEQ ID NO: 104 | CAGGCGGGTCTGGGCgatTATTCTatTTCTGGCCTG |
| Met302 | SEQ ID NO: 105 | CAGGCGGGTCTGGGCatgTATTCTatTTCTGGCCTG |
| Thr302 | SEQ ID NO: 106 | CAGGCGGGTCTGGGCaccTATTCTatTTCTGGCCTG |
| Gln302 | SEQ ID NO: 107 | CAGGCGGGTCTGGGCcagTATTCTatTTCTGGCCTG |
| Arg302 | SEQ ID NO: 108 | CAGGCGGGTCTGGGCcgtTATTCTatTTCTGGCCTG |
| Ser302 | SEQ ID NO: 109 | CAGGCGGGTCTGGGCagcTATTCTatTTCTGGCCTG |

2: Preparation of *Escherichia coli* Expressing Dehalogenase Variant

An EcoRI site was digested from a pMAL-c2 vector (available from New England Biolabs Inc.). The two amplified products prepared in Example 1 were inserted into the site of the pMAL-c2 vector from which EcoRI site was digested using In-Fusion® HD Cloning plus (available from TaKaRa Cat No.638909.). Accordingly, a pMAL-c2-CfrA-mut vector was obtained, which expresses a dehalogenase variant. By sequencing, it was verified that the gene encoding the dehalogenase variant was introduced into the vector. This vector was introduced into an *Escherichia coli* BL21 Star strain by a heat shock method. The *Escherichia coli* (*E. Coli*) strain into which the gene encoding the dehalogenase variant was introduced was named '*E. coli* BL21 star/pMAL-c2-CfrA-mut'.

As a control or negative control (NC), *E. coli* into which a gene encoding a dehalogenase was introduced was prepared in substantially the same manner as above, except that a polynucleotide having the nucleotide sequence of SEQ ID NO: 2 was inserted into a pMAL-c2 vector as a gene encoding a dehalogenase. The *E. coli* into which the gene encoding a dehalogenase was introduced was named '*E. coli* BL21 star/pMAL-c2-CfrA-wt'. In addition, *E. coli* into which a pMAL-c2 vector was introduced was prepared in substantially the same manner as above, except that an unmodified pMAL-c2 vector was inserted thereinto. This *E. coli* into which the unmodified pMAL-c2 vector was introduced was named '*E. coli* BL21 star/pMAL-c2'.

3: Decomposition of Fluorinated Methane by Dehalogenase Variant

It was verified whether the *E. coli* expressing a dehalogenase variant had decomposition activity with respect to fluorinated methane ($CF_4$).

The *E. coli* BL21 star/pMAL-c2-CfrA-mut obtained in Example 2 was inoculated in a medium in a shaking incubator, incubated in the presence of 0.2 mM of isopropyl-β-D-thiogalactopyranoside (IPTG) and 1 μM of a cobalamin cofactor at a temperature of 20° C. for 20 hours to induce expression of the gene encoding a dehalogenase variant. A cell pellet was obtained from the culture medium, and lysed in PBS buffer (available from Sigma-Aldrich Inc.) to obtain a lysate. A crude extract was obtained from the lysate. Next, 2 mM Ti(III)-NTA, 2 mM methylviologen, and 5 ml of the crude extract were added to a serum bottle, and $CF_4$ was added to a headspace at a concentration of 1,000 ppm. The bottle was sealed and incubated at 30° C. for a predetermined time.

Once the incubation was complete, an amount of $CF_4$ in the headspace was analyzed. For analysis, 0.5 ml was collected from the headspace using a syringe and injected into GC (Agilent 7890, Palo Alto, Calif., USA). The injected $CF_4$ was separated through a CP-PoraBOND Q column (25 m length, 0.32 mm i.d., 5 um film thickness, Agilent), and changes in concentration of the separated $CF_4$ were analyzed by MSD (Agilent 5973, Palo Alto, Calif., USA). As a carrier gas, helium was applied to the column at a flow rate of 1.5 ml/min. GC conditions were as follows: An inlet temperature was 250° C., an initial temperature was maintained at 40° C. for 2 minutes, and temperature was raised to 290° C. at a rate of 20° C./min. MS conditions were as follows: ionization energy was 70 eV, an interface temperature was 280° C., an ion source temperature was 230° C., and a quadrupole temperature was 150° C. *E. coli* BL21 star/pMAL-c2-CfrA-wt or *E. coli* BL21 star/pMAL-c2, i.e., a NC, was incubated in substantially the same manner as above, followed by incubation with $CF_4$ and analysis of the amount of $CF_4$ in the headspace.

3-1: Decomposition of Fluorinated Methane by *E. coli* Expressing Dehalogenase Variant having Amino Acid Alteration at R305

Recombinant *E. coli* cells (*E. coli* BL21 star/pMAL-c2-CfrA-mut-R305X) expressing a dehalogenase variant and having an amino acid sequence of SEQ ID NO: 1 substituted with 19 different amino acids at R305 were used, and an amount of $CF_4$ was analyzed in substantially the same manner as in Example 3.

Figure 2:
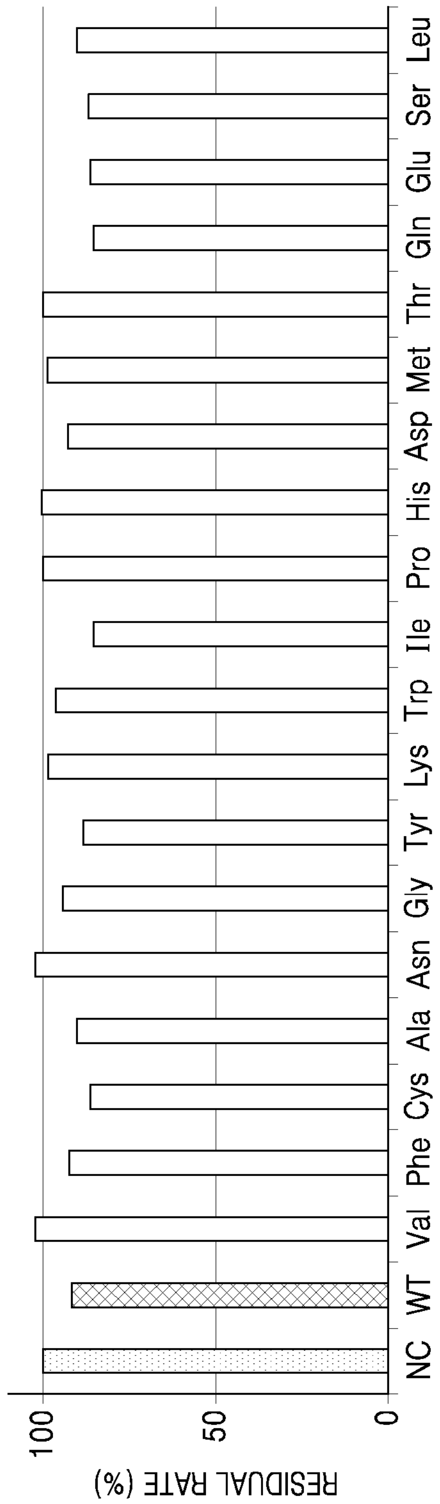
FIG. 2 is a bar graph illustrating degrees of decomposition of $CF_4$ by dehalogenase variants having an amino acid sequence of SEQ ID NO: 1 substituted with the indicated amino acid at position R305. Data is provided in terms of a residual ratio (percentage, %) of $CF_4$.

FIG. 2 is a bar graph of illustrating a degree of decomposition of $CF_4$ by an NC and the recombinant *E. coli* cells in terms of a residual ratio (percentage, %) of $CF_4$. Changes in the $CF_4$ concentration were normalized using the NC value. As shown in FIG. 2, the dehalogenase variant of SEQ ID NO: 1 having the amino acid residue corresponding to position R305 substituted with I, Q, E, S, C, or Y was found to reduce the amount of $CF_4$ more than the NC. Referring to FIG. 2, the dehalogenase variant was found to have increased activity of decomposition of $CF_4$, as compared with the NC.

Table 9 shows a degree of decomposition of $CF_4$, in terms of a rate and activity of decomposition, by recombinant *E. coli* cells expressing dehalogenase variants each having an amino acid sequence of SEQ ID NO: 1 substituted with I, Q, E, or S at the amino acid residue corresponding to position R305.

As shown in Table 9, each of the dehalogenase variants having an amino acid sequence of SEQ ID NO: 1 substituted with I, Q, E, or S at the amino acid residue corresponding to position R305 was found to reduce the amount of $CF_4$ by about 16% or greater, as compared with the NC. In addition, each of the dehalogenase variants having an amino acid sequence of SEQ ID NO: 1 substituted with I, Q, E, or S at the amino acid residue corresponding to position R305 was found to have an increase in activity of decomposition of $CF_4$ of about 15% or greater, as compared with the NC. In this case, the term "activity" refers to the number of μmols of $CF_4$ that can be decomposed by 1 g of cells of a recombinant microorganism expressing a dehalogenase or a dehalogenase variant for 1 minute.

TABLE 9

| Amino acid alteration | Used recombinant *E. coli* | $CF_4$ decomposition rate (%) | Activity (μmol/gcell · min) |
|---|---|---|---|
| R305 | *E. coli* BL21 star/pMALc2-CfrA-wt | 8.3 | 0.0030 |
| R305I | *E. coli* BL21 star/pMALc2-CfrA-mut-R305I | 14.3 | 0.0052 |
| R305Q | *E. coli* BL21 star/pMALc2-CfrA-mut-R305Q | 13.3 | 0.0048 |
| R305E | *E. coli* BL21 star/pMALc2-CfrA-mut-R305E | 13.4 | 0.0049 |
| R305S | *E. coli* BL21 star/pMALc2-CfrA-mut-R305S | 13 | 0.0047 |

3-2: Decomposition of Fluorinated Methane by *E. coli* Expressing Dehalogenase Variant having Amino Acid Alteration at A184

Recombinant *E. coli* cells (*E. coli* BL21 star/pMAL-c2-CfrA-mut-A184X) expressing a dehalogenase variant having an amino acid sequence of SEQ ID NO: 1 substituted with 19 different amino acids at A184 were used, and an amount of $CF_4$ was analyzed in substantially the same manner as in Example 3.

3-3: Decomposition of Fluorinated Methane by *E. coli* Expressing Dehalogenase Variant having Amino Acid Alteration at Y279

Recombinant *E. coli* cells (*E. coli* BL21 star/pMAL-c2-CfrA-mut-Y279X) expressing a dehalogenase variant having an amino acid sequence of SEQ ID NO: 1 substituted with 19 different amino acids at Y279 were used, and an amount of $CF_4$ was analyzed in substantially the same manner as in Example 3.

3-4: Decomposition of Fluorinated Methane by *E. coli* Expressing Dehalogenase Variant having Amino Acid Alteration at E302

Recombinant *E. coli* cells (*E. coli* BL21 star/pMAL-c2-CfrA-mut-E302X) expressing a dehalogenase variant having an amino acid sequence of SEQ ID NO: 1 substituted with 19 different amino acids at E302 were used, and an amount of $CF_4$ was analyzed in substantially the same manner as in Example 3.

Figure 3:
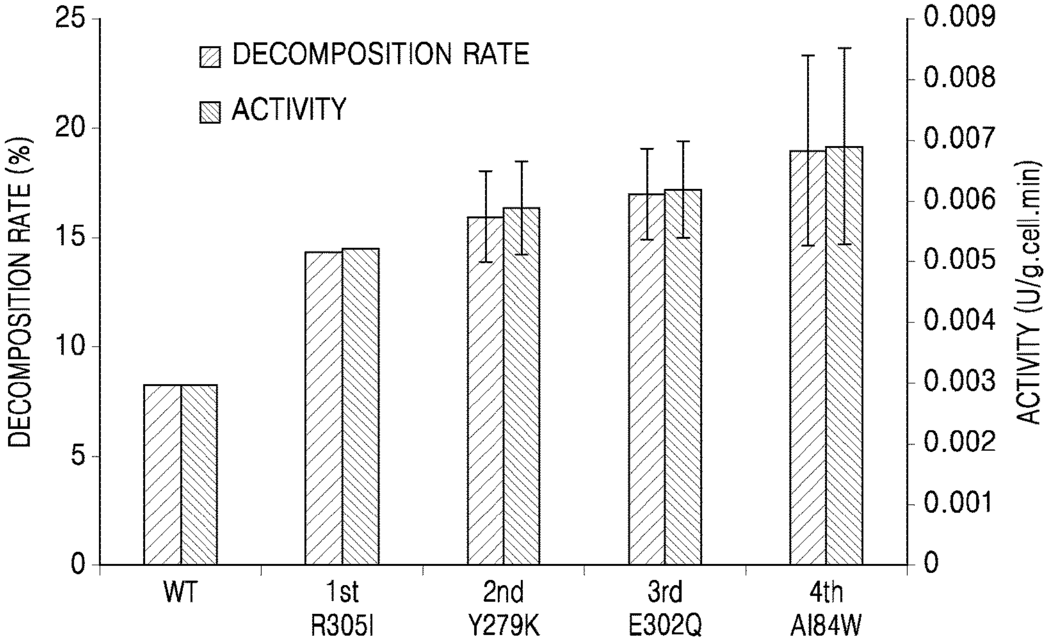
FIG. 3 is a bar graph of activity (U/g.cell.min) and $CF_4$ decomposition rate (%) by a dehalogenase of SEQ ID NO: 1 with a substitution of A184W, Y279K, E302Q, or R305I. The decomposition rate (%) represents a value obtained from the formula: (Δ peak area/peak area of control)×100, and Δ peak area represents a value obtained from a formula: (peak area of control-peak area of dehalogenase variant)

Table 10 and FIG. 3 show the results of Examples 3-2 to 3-4, regarding a degree of decomposition of $CF_4$ in terms of a rate and activity of decomposition by the NC and the recombinant *E. coli* cells expressing the dehalogenase variants.

TABLE 10

| | Amino acid alteration | Used recombinant *E. coli* | Decomposition rate (%) | Activity (U/gcell · min) |
|---|---|---|---|---|
| WT | — | *E. coli* BL21 star/pMALc2-CfrA-wt | 8.3 | 0.003 |
| 1st | R305I | *E. coli* BL21 star/pMALc2-CfrA-mut-R305I | 14.3 | 0.0052 |
| 2nd | Y279K | *E. coli* BL21 star/pMALc2-CfrA-mut-Y279K | 16 | 0.0059 |
| 3rd | E302Q | *E. coli* BL21 star/pMALc2-CfrA-mut-E302Q | 17 | 0.0062 |
| 4th | A184W | *E. coli* BL21 star/pMALc2-CfrA-mut-A184W | 19 | 0.0069 |

Referring to the results of Table 10 and FIG. 3, the dehalogenase variants were found to have a rate and activity of decomposition two times greater than those of a dehalogenase having the amino acid sequence of SEQ ID NO: 1 without an amino acid substitution.

4-4: Decomposition of Fluorinated Methane by *E. coli* Expressing Dehalogenase Variant having Amino Acid Alteration at A184, Y279, E302, and R305

Degrees of decomposition of $CF_4$ by an NC; a dehalogenase variant having A184W, Y279K, E302Q, and R305I substitutions in an amino acid sequence of SEQ ID NO: 1 (hereinafter referred as 'pMAL-c2-CfrA-mut-A184W-Y279K-E302Q-R305I or eCfrA'); the control and P450-BM3; and the dehalogenase variant and P450-BM3 were measured in substantially the same manner as in Example 3. The dehalogenase variant having A184W, Y279K, E302Q, and R305I substitutions in an amino acid sequence of SEQ ID NO: 1 had an amino acid sequence of SEQ ID NO: 110 and a nucleotide sequence of SEQ ID NO: 111.

Figure 4:
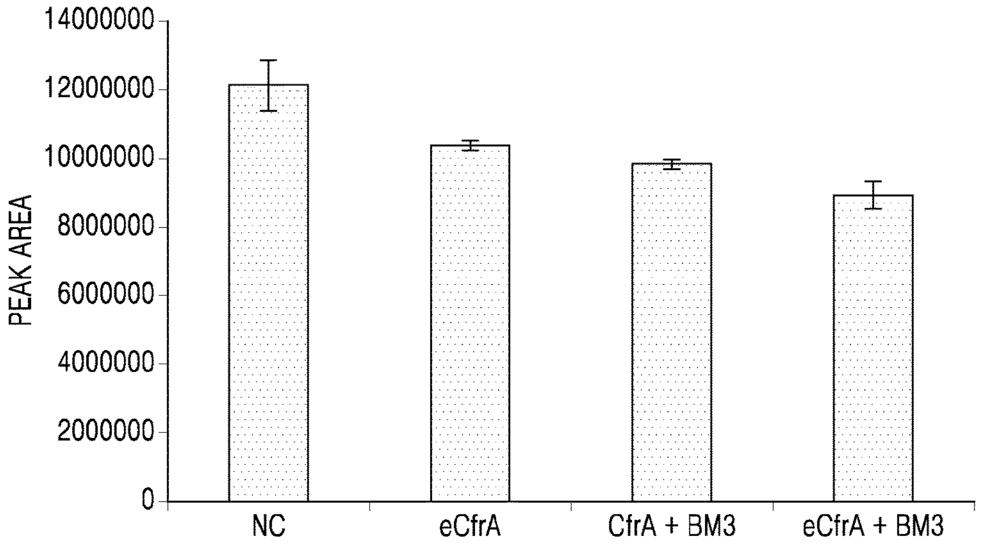
FIG. 4 is a bar graph showing the residual rate of $CF_4$ by a control dehalogenase or a dehalogenase variant having a substitution of A184W, Y279K, E302Q, and R305I in an amino acid sequence of SEQ ID NO: 1; a control dehalogenase and P450-BM3; and the dehalogenase variant and P450-BM3. The vertical axis represents peak area.

As shown in FIG. 4, when the amino acid sequence of SEQ ID NO: 1 substituted with all of A184W, Y279K, E302Q, and R305I was used, the decomposition rate thereof was about 20%. In addition, when the recombinant *E. coli* expressing both the dehalogenase variant and P450-BM3 was used, the $CF_4$ decomposition rate thereof was about 27%. In other words, the dehalogenase variant was found to have increased $CF_4$ decomposition activity due to having four amino acid substitutions, and $CF_4$ decomposition activity of the dehalogenase variant was maintained even in combination with a different dehalogenase.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A dehalogenase variant having dehalogenase activity and comprising an amino acid sequence comprising 95% sequence to SEQ ID NO: 1 and one or more substitutions in SEQ ID NO: 1 selected from the group consisting of A184W, Y279K, E302Q, R305I, R305E, and R305S.

2. A method of reducing $CH_nF_{4-n}$ concentration in a sample, the method comprising contacting a sample comprising $CH_nF_{4-n}$ with the dehalogenase variant of claim 1 to reduce the $CH_nF_{4-n}$ concentration in the sample, wherein n is an integer from 0 to 3.

3. The method of claim 2, wherein the dehalogenase variant is in a recombinant microorganism comprising an exogenous polynucleotide encoding the dehalogenase variant, a lysate thereof, or a fraction of the lysate thereof.

4. The method of claim 2, wherein contacting the sample with the dehalogenase variant comprises culturing or incubating a recombinant microorganism comprising an exogenous polynucleotide encoding the dehalogenase variant, a lysate thereof, or a fraction of the lysate thereof with the sample.

5. The method of claim 2, wherein contacting the sample with the dehalogenase variant is performed in a sealed container.

6. The method of claim 2, wherein the sample is a liquid or a gas.

7. The method of claim 2, wherein $CH_nF_{4-n}$ is $CF_4$, $CHF_3$, or $CH_2F_2$.

* * * * *